United States Patent [19]

Schulz et al.

[11] Patent Number: 5,466,576
[45] Date of Patent: Nov. 14, 1995

[54] MODULATION OF PIF-1-TYPE HELICASES

[75] Inventors: Vincent P. Schulz; Virginia A. Zakian, both of Seattle, Wash.

[73] Assignee: Fred Hutchinson Cancer Research Center, Seattle, Wash.

[21] Appl. No.: 86,993

[22] Filed: Jul. 2, 1993

[51] Int. Cl.$^6$ .............................. C12Q 1/68; C12N 9/00; C12N 9/10; C12N 15/54
[52] U.S. Cl. .............................. 435/6; 435/183; 435/193; 935/8; 935/28
[58] Field of Search ................................ 435/6, 183, 193; 935/8, 28

[56] References Cited

U.S. PATENT DOCUMENTS

| | | | |
|---|---|---|---|
| 5,190,762 | 3/1993 | Yarosh | 424/450 |
| 5,217,864 | 6/1993 | Heintz | 435/6 |

OTHER PUBLICATIONS

Van Dyck et al. "A single stranded DNA Binding Protein Required for Mitochondrial DNA Replication in *S. cerevisiae* is Homologous to *E coli* SSB." EMBOJ 11(9) 3421–3430 1992.
Lahaye et al. "PIF1: A DNA helicase In Yeast Mitochondria" EMBOJ. 10(4): 997–1007 1991.
Lahue et al. "*E coli* DNA Helicase I Catalyzes A Unidirectional & Highly Processive Unwinding Reaction" J Biol Chem. 263(7) 3208–3215 1988.
Murphy "λ Gam Protein Inhibits the Helicase and X–Stimulated Recombination Activities of *E coli* RecBCD Enzyme" J. Bacteriol 173(18): 5808–5821 1991.
Lahaye et al. "Pif1 Is a Potential Mitochondrial DNA Helicase" Yeast (6): S524 1990.
Goldstein, "Replicative Senescence: The Human Fibroblast Comes of Age", 249 *Science* 1129, 1990.
Hayflick and Moorehead, "The Serial Cultivation of Human Diploid Cell Strains", 25 *Exp. Cell Res.*, 585, 1961.
Ohno, "Strict Relationship Between Dialyzed Serum Concentration and Cellular Life Span *In Vitro*, "11 *Mech. Aging Dev.* 179, 1979.
Ham and McKeehan, "Media and Growth Requirements", W. B. Jacoby and I. M. Pastan (eds), in: 58 *Methods in Enzymology*, Academic Press, N.Y., 44–93, 1979.
Martin et al., "Replicative Life–Span of Cultivated Human Cells", 23 *Lab. Invest.*, 86, 1979.
Goldstein et al., "Diabetes Mellitus and Aging: Diminished Plating Efficiency of Cultured Human Fibroblasts", *Proc. Natl. Acad. Sci. USA* 155, 1969.
Shay et al., "A Role for Both RB and p53 in the Regulation of Human Cellular Senescence", *Exp. Cell REs.* 33, 1991.
Shay and Wright, "Quantitation of the Frequency of Immortalization of Normal Human Diploid Fibroblasts by SV40 Large T–Antigen", 184 *Exp. Cell Res.* 109, 1989.
Shay et al., "Re–Expression of Senescent Markers in Deinduced Reversibly Immortalized Cells", *Experimental Gerontology* 477, 1992.
Harley et al., "Telomeres Shorten During Ageing of Human Fibroblasts", 345 *Nature* 458, 1990.
Hastie et al., "Telomere Reduction in Human Colorectal Carcinoma and With Ageing", 346 *Nature* 866, 1990.
Harley, "Telomere Loss: Mitotic Clock or Genetic Time Bomb?", 256 *Mutation Research* 271, 1991.
DeLange et al., "Structure and Variability of Human Chromosome Ends", 10 *Molecular and Cellular Biology* 518, 1990.
Starling et al., "Extensive Telomere Repeat Arrays in Mouse are Hypervariable", 18 *Nucleic Acids Research* 6881, 1990.
D'Mello and Jazwinski, "Telomere Length Constancy during Aging of *Saccharomyces cerevisiae*", 173 *J. Bacteriology* 6709, 1990.

(List continued on next page.)

*Primary Examiner*—Michael G. Wityshyn
*Assistant Examiner*—Nancy J. Degen

[57] ABSTRACT

Method for affecting viability of a eucaryotic cell by contacting the cell with a modulator of the activity of a PIF-1-type helicase in the cell. Such contacting specifically increases or decreases the specific activity of the helicase in the cell.

8 Claims, 7 Drawing Sheets

OTHER PUBLICATIONS

Hiyama et al., "Length of Telomeric Repeats in Neuroblastoma: Correlation with Prognosis and Other Biological Characteristics", 83 *Jpn J. Cancer Res.* 159, 1992.

Counter et al., "Telomere shortening associated with chromosome instability is arrested in immortal cells which express telomerase activity", 11 *EMBO J.* 1921, 1992.

Levy et al., "Telomere End–replication Problem and Cell Aging", 225 *J. Mol. Biol.* 951, 1992.

Windle and McGuire, "Telomeres: The Long and The Short of It", 33 *Proceedings of the American Association for Cancer Research*, 594, 1992.

Greider, "Telomeres, Telomerase and Senescence", 12 *BioEssays* 363, 1990.

Greider and Blackburn, "A telomeric sequence in the RNA of Tetrahymena telomerase required for the telomere repeat synthesis", 337 *Nature* 331, 1989.

Wellinger et al., "Saccharomyces Telomeres Acquire Single–Strand $TG_{1-3}$ Tails Late in S Phase", 72 *Cell* 51, 1993.

Watson, "Origin of Concatemeric T7 DNA", 239 *Nature* 197, 1972.

Greider, "Telomerase Is Processive", 11 *Mol. Cell Biol.* 4572, 1991.

Yu and Blackburn, "Developmentally Programmed Healing of Chromosomes by Telomerase in Tetrahymena", 67 *Cell* 823, 1991.

Murray and Szostak, "Construction of artificial chromosomes in yeast", 305 *Nature* 189, 1983.

Pluta et al., "Elaboration of telomeres in yeast: Recognition and modification of termini from Oxytricha macronuclear DNA", 81 *Proc. Natl. Acad Sci.* 1475, 1984.

Greider and Blackburn, "Identification of a Specific Telomere Terminal Transferase Activity in Tetrahymena Extracts" 43 *Cell* 405, 1985.

Pluta and Zakian, "Recombination occurs during telomere formation in yeast", 337 *Nature* 429, 1989.

Wang and Zakian, "Telomere–telomere recombination provides an express pathway for telomere acquisition", 345 *Nature* 456, 1990.

Greider and Blackburn, "The Telomere Terminal Transferase of Tetrahymena Is a Ribonucleoprotein Enzyme with Two Kinds of Primer Specificity", 51 *Cell* 887, 1987.

Gottshling et al., "Position Effect at *S. cerevisiae* Telomeres: Reversible Repression of Pol II Transcription", 63 *Cell* 751, 1990.

Wright et al., "Saccharomyces telomeres assume a non–nucleosomal chromatin structure", 6 *Genes & Dev.* p. 1987, 1992.

Klein et al., "Localization of RAP1 and Topoisomerase II in Nuclei and Meiotic Chromosomes of Yeast", 117 *J. Cell Biol.* 935, 1992.

De Lange, "Human telomeres are attached to the nuclear matrix", 11 *EMBO J.* 717, 1992.

Buchman et al., "Connections between Transcriptional Activators, Silencers, and Telomeres as Revealed by Functional Analysis of a Yeast DNA–Binding Protein", 8 *Mol. Cell Biol.* 5086–99, 1988.

Longtine, "A yeast Telomere Binding Activity binds to two related telomere sequence motifs and is indistinguishable from RAP1", 16 *Curr. Genet.* 225, 1989.

Conrad et al., "RAP1 Protein Interacts with Yeast Telomeres In Vivo: Overproduction Alters Telomere Structure and Decreases Chromosome Stability", 63 *Cell* 739, 1990.

Lustig et al., "Involvement of the Silencer and UAS Binding Protein RAP1 in Regulation of Telomere Length", 250 *Science* 549, 1990.

Sussel and Shore, "Separation of transcriptional activation and silencing functions of the RAP1–encoded repressor/activator protein1: Isolation of viable mutants affecting both silencing and telomere length", 88 *Proc. Natl. Acad. Sci.* 7749, 1991.

Kyrion et al., "C–Terminal Truncation of RAP1 Results in the Deregulation of Telomere Size, Stability, and Function in *Saccharomyces cerevisiae*", 12 *Mol. Cell. Biol.* 5159, 1992.

Hardy et al., "A RAP1–interacting protein involved in transcriptional silencing and telomere length regulation", *Genes & Dev.* 801, 1992.

Carson and Hartwell, "CDC–17: An Essential Gene That Prevents Telomere Elongation in Yeast". 42 *Cell* 249, 1985.

Lustin and Petes, "Identification of yeast mutants with altered telomere structure", 83 *Proc. Natl. Acad. Sci.* 1398, 1986.

Lundblad and Szostak, "A Mutant with a Defect in Telomere Elongation Leads to Senescence in Yeast", 57 *Cell* 633, 1989.

Bachur et al., "Helicase Inhibition by Anthracycline Anticancer Agents", 41 *Mol. Pharm.* 993, 1992.

FIG. 4B

| | PIF1 | | pif1-m2 | | tst1-1 | | pif1Δ | |
|---|---|---|---|---|---|---|---|---|
| | % | rate | % | rate | % | rate | % | rate |
| >4.7 kbp deletion | 3 | $3 \times 10^{-8}$ | 52 | $2 \times 10^{-5}$ | 92 | $2 \times 10^{-4}$ | 75 | $4 \times 10^{-4}$ |
| $C_4A_4$ | 76 | $8 \times 10^{-7}$ | 40 | $1 \times 10^{-5}$ | 8 | $1 \times 10^{-5}$ | 25 | $2 \times 10^{-4}$ |
| Point mutation | 22 | $2 \times 10^{-7}$ | 8 | $3 \times 10^{-6}$ | 0 | — | 0 | — |

FIG. 6B

| strain: | PIF1 RIF1 | pif1-m2 RIF1 | PIF1 rif1Δ | pif1-m2 rif1Δ |
|---|---|---|---|---|
| LEU+, FOA^R | 1.2 | 35 | 0.72 | 8.6 |
| Fold Increase | (1) | 30 | 0.6 | 7.2 |

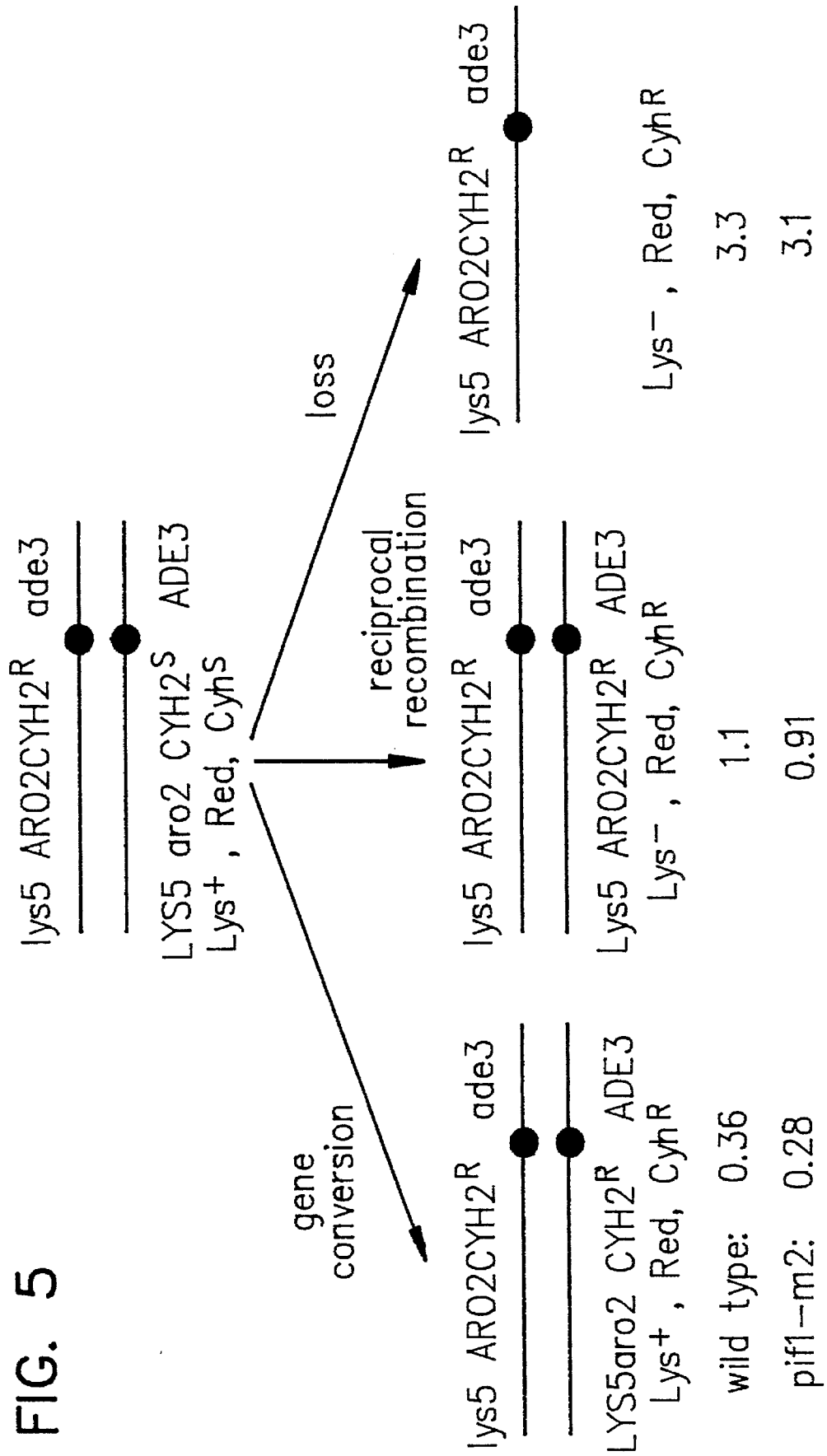

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 1:

ATCAATTTTG GGCCCCAAAG TGG         2 3

( 2 ) INFORMATION FOR SEQ ID NO: 2:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 2:

TCGTTTTCTG CCTCGAGTCG TGGT  24

MODULATION OF PIF-1-TYPE HELICASES

The invention described in this application may have had U.S. government support from National Institutes of Health grants GM-26938 and GM-43265. The U.S. government may have certain rights in the invention.

BACKGROUND OF THE INVENTION

This invention relates to methods for affecting viability of eucaryotic cells.

Normal human somatic cells (e.g., fibroblasts, endothelial, and epithelial cells) display a finite replicative capacity of 50–100 population doubling characterized by a cessation of proliferation in spite of the presence of abundant growth factors. This cessation of replication in vitro is variously referred to as cellular senescence or cellular aging, See, Goldstein, 249 *Science* 1129, 1990; Hayflick and Moorehead, 25 *Exp. Cell Res.* 585, 1961; Hayflick, ibid., 37:614, 1985; Ohno, 11 *Mech. Aging Dev.* 179, 1979; Ham and McKeehan, (1979) "Media and Growth Requirements", W. B. Jacoby and I. M. Pastan (eds), in: *Methods in Enzymology*, Academic Press, N.Y., 58:44–93. The replicative life span of cells is inversely proportional to the in vivo age of the donor (Martin et al., 23 *Lab. Invest.* 86, 1979; Goldstein et al., 64 *Proc. Natl. Acad. Sci. USA* 155, 1969; and Schneider and Mitsui, ibid., 73:3584, 1976), therefore cellular senescence is suggested to play an important role in aging in vivo.

Cellular immortalization (the acquisition of unlimited replicative capacity) may be thought of as an abnormal escape from cellular senescence, Shay et al., 196 *Exp. Cell Res.* 33, 1991. Normal human somatic cells appear to be mortal, i.e., have finite replicative potential. In contrast, the germ line and malignant tumor cells are immortal (have indefinite proliferative potential). Human cells cultured in vitro appear to require the aid of transforming viral oncoproteins to become immortal and even then the frequency of immortalization is $10^{-6}$ to $10^{-7}$. Shay and Wright, 184 *Exp. Cell Res.* 109, 1989.

Shay et al., 27 *Experimental Gerontology* 477, 1992, and 196 *Exp. Cell Res.* 33, 1991 describe a two-stage model for human cell mortality to explain the ability of Simian Virus 40 T-antigen to immortalize human cells. The mortality stage 1 mechanism (M1) is the target of certain tumor virus proteins, and an independent mortality stage 2 mechanism (M2) produces crisis and prevents these tumor viruses from directly immortalizing human cells. The authors utilized T-antigen driven by a mouse mammary tumor virus promoter to cause reversible immortalization of cells. The Simian Virus 40 T-antigen is said to extend the replicative life span of human fibroblast by an additional 40–60%. The authors postulate that the M1 mechanism is overcome by T-antigen binding to various cellular proteins, or inducing new activities to repress the M1 mortality mechanism. The M2 mechanism then causes cessation of proliferation, even though the M1 mechanism is blocked. Immortality is achieved only when the M2 mortality mechanism is also disrupted.

Harley et al., 345 *Nature* 458, 1990, state that the amount and length of telomeric DNA in human fibroblasts decreases as a function of serial passage during aging in vitro, and possibly in vivo, but do not know whether this loss of DNA has a causal role in senescence. They also state:

"Tumour cells are also characterized by shortened telomeres and increased frequency of aneuploidy, including telomeric associations. If loss of telomeric DNA ultimately causes cell-cycle arrest in normal cells, the final steps in this process may be blocked in immortalized cells. Whereas normal cells with relatively long telomeres and a senescent phenotype may contain little or no telomerase activity, tumour cells with short telomeres may have significant telomerase activity. Telomerase may therefore be an effective target for anti-tumour drugs.

There are a number of possible mechanisms for loss of telomeric DNA during ageing, including incomplete replication, degradation of termini (specific or nonspecific), and unequal recombination coupled to selection of cells with shorter telomeres. Two features of our data are relevant to this question. First, the decrease in mean telomere length is about 50 bp per mean population doubling and, second, the distribution does not change substantially with growth state or cell arrest. These data are most easily explained by incomplete copying of the template strands at their 3' termini. But the absence of detailed information about the mode of replication or degree of recombination at telomeres means that none of these mechanisms can be ruled out. Further research is required to determine the mechanism of telomere shortening in human fibroblasts and its significance to cellular senescence." [Citations omitted.]

Hastie et al., 346 *Nature* 866, 1990, while discussing colon tumor cells, state that:

"[T]here is a reduction in the length of telomere repeat arrays relative to the normal colonic mucosa from the same patient.

Firm figures are not available, but it is likely that the tissues of a developed fetus result from 20–50 cell divisions, whereas several hundred or thousands of divisions have produced the colonic mucosa and blood cells of 60-year old individuals. Thus the degree of telomere reduction is more or less proportional to the number of cell divisions. It has been shown that the ends of Drosophila chromosomes without normal telomeres reduce in size by 4 base pairs (bp) per cell division and that the ends of yeast chromosomes reduce by a similar degree in a mutant presumed to lack telomerase function. If we assume the same rate of reduction is occurring during somatic division in human tissues, then a reduction in TRA by 14 kb would mean that 3,500 ancestral cell divisions lead to the production of cells in the blood of a 60-year old individual; using estimates of sperm telomere length found elsewhere we obtain a value of 1,000–2,000. These values compare favourably with those postulated for mouse blood cells. Thus, we propose that telomerase is indeed lacking in somatic tissues. In this regard it is of interest to note that in maize, broken chromosomes are only healed in sporophytic (zygotic) tissues and not in endosperm (terminally differentiated), suggesting that telomerase activity is lacking in the differentiated tissues." [Citations omitted.]

The authors propose that in some tumors telomerase is reactivated, as proposed for HeLa cells in culture, which are known to contain telomerase activity. But, they state:

"One alternative explanation for our observations is that in tumours the cells with shorter telomeres have a growth advantage over those with larger telomeres, a situation described for vegetative cells of tetrahymena." [Citations omitted.]

Harley, 256 *Mutation Research* 271, 1991, discusses observations allegedly showing that telomeres of human somatic cells act as a mitotic clock shortening with age both in vitro and in vivo in a replication dependent manner. He states:

"Telomerase activation may be a late, obligate event in immortalization since many transformed cells and tumour tissues have critically short telomeres. Thus, telomere length and telomerase activity appear to be markers of the replicative history and proliferative potential of cells; the intriguing possibility remains that telomere loss is a genetic time bomb and hence causally involved in cell senescence and immortalization.

Despite apparently stable telomere length in various tumour tissues or transformed cell lines, this length was usually found to be shorter than those of the tissue of origin. These data suggest that telomerase becomes activated as a late event in cell transformation, and that cells could be viable (albeit genetically unstable) with short telomeres stably maintained by telomerase. If telomerase was constitutively present in a small fraction of normal cells, and these were the ones which survived crisis or became transformed, we would expect to find a greater frequency of transformed cells with long telomeres." [Citations omitted.]

He proposes a hypothesis for human cell aging and transformation as "[a] semi-quantitative model in which telomeres and telomerase play a causal role in cell senescence and cancer" and proposes a model for this hypothesis.

De Lange et al., 10 *Molecular and Cellular Biology* 518, 1990, generally discuss the structure of human chromosome ends or telomeres. They state:

"we do not know whether telomere reduction is strictly coupled to cellular proliferation. If the diminution results from incomplete replication of the telomere, such a coupling would be expected; however, other mechanisms, such as exonucleolytic degradation, may operate independent of cell division. In any event, it is clear that the maintenance of telomeres is impaired in somatic cells. An obvious candidate activity that may be reduced or lacking is telomerase. A human telomerase activity that can add TTAGGG repeats to G-rich primers has recently been identified (G. Morin, personal communication). Interestingly, the activity was demonstrated in extracts of HeLa cells, which we found to have exceptionally long telomeres. Other cell types have not been tested yet, but such experiments could now establish whether telomerase activity is (in part) responsible for the dynamics of human chromosome ends."

Starling et al., 18 *Nucleic Acids Research* 6881, 1990, indicate that mice have large telomeres and discusses this length in relationship to human telomeres. They state:

"Recently it has been shown that there is reduction in TRA length with passage number of human fibroblasts in vitro and that cells in a senescent population may lack telomeres at some ends altogether. Thus in vitro, telomere loss may play a role in senescence, a scenario for which there is evidence in *S. cerevisae* and Tetrahymena. Some of the mice we have been studying are old in mouse terms, one and a half years, yet they still have TRA's greater than 30 kb in all tissues studied. In humans, telomeres shorten with age at a rate of 100 bp per year, hence, it is conceivable that the same is happening in the mouse, but the removal of a few 100 bps of terminal DNA during its lifetime would not be detectable." [Citations omitted.]

D'Mello and Jazwinski, 173 *J. Bacteriology* 6709, 1991, state:

"We propose that during the life span of an organism, telomere shortening does not play a role in the normal aging process. However, mutations or epigenetic changes that affect the activity of the telomerase, like any other genetic change, might affect the life span of the individual in which they occur.

In summary, the telomere shortening with age observed in human diploid fibroblasts may not be a universal phenomenon. Further studies are required to examine telomere length and telomerase activity not only in different cell types as they age but also in the same cell type in different organisms with differing life spans. This would indicate whether telomere shortening plays a causal role in the senescence of a particular cell type or organism."

Hiyama et al., 83 *Jpn. J. Cancer Res.* 159, 1992, provide findings that "suggest that the reduction of telomeric repeats is related to the proliferative activity of neuroblastoma cells and seems to be a useful indicator of the aggressiveness of neuroblastoma... Although we do not know the mechanism of the reduction and the elongation of telomeric repeats in neuroblastoma, we can at least say that the length of telomeric repeats may be related to the progression and/or regression of neuroblastoma."

Counter et al., 11 *EMBO J.* 1921, 1992, state "loss of telomeric DNA during cell proliferation may play a role in ageing and cancer." They propose that the expression of telomerase is one of the events required for a cell to acquire immortality and note that:

This model may have direct relevance to tumourigenesis in vivo. For example, the finite lifespan of partially transformed (pre-immortal) cells which lack telomerase might explain the frequent regression of tumours after limited growth in vivo. In bypassing the checkpoint representing normal replicative senescence, transformation may confer an additional 20–40 population doubling during which an additional ≈2 kbp of telomeric DNA is lost. Since 20–40 doubling ($10^6$–$10^{12}$ cells in a clonal population) potentially represents a wide range of tumour sizes, it is possible that many benign tumours may lack telomerase and naturally regress when telomeres become critically shortened. We predict that more aggressive, perhaps metastatic tumours would contain immortal cells which express telomerase. To test this hypothesis, we are currently attempting to detect telomerase in a variety of tumour tissues and to correlate activity with proliferative potential. Anti-telomerase drugs or mechanisms to repress telomerase expression could be effective agents against tumours which depend upon the enzyme for maintenance of telomeres and continued cell growth.

Levy et al., 225 *J. Mol. Biol.* 951, 1992, state that:

"Although it has not been proven that telomere loss contributes to senescence of multicellular organisms, several lines of evidence suggest a causal relationship may exist.

It is also possible that telomere loss with age is significant in humans, but not in mice." [Citations omitted.]

Windle and McGuire, 33 *Proceedings of the American Association for Cancer Research* 594, 1992, discuss the role of telomeres and state that:

"These and other telomere studies point in a new direction regarding therapeutic targets and strategies to combat cancer. If the cell can heal broken chromosomes preventing genomic disaster, then there may be a way to facilitate or artificially create this process. This could even provide a preventive means of stopping cancer which could be particularly applicable in high risk patients. The difference in telomere length in normal versus tumor cells also suggests a strategy where the loss of telomeres is accelerated. Those cells with the shortest telomeres, such as those of tumor metastasis would be the most susceptible."

Greider, 12 *BioEssays* 363, 1990, provides a review of the relationship between telomeres, telomerase, and senescence. She indicates that telomerase contains an RNA component which provides a template for telomere repeat synthesis. She notes that an oligonucleotide "which is complementary to the RNA up to and including the CAACCCCAA sequence, competes with d(TTGGGG)n primers and inhibits telomerase in vitro" (citing Greider and Blackburn, 337 *Nature* 331, 1989). She also describes experiments which she believes "provide direct evidence that telomerase is involved in telomere synthesis in vivo."

Telomeric DNA is usually composed of a simple repetitive sequence, with the strand running 5' to 3' from the end towards the center of the chromosome being C and A rich. For example, the telomeric sequence of the yeast *S. cerevisiae* is $C_{1-3}A/TG_{1-3}$, and that of the ciliate Oxytricha is $C_4A_4/T_4G_4$. The G-strand is extended to form a 12 to 16 base tail on some or all of the subchromosomal macronuclear DNA molecules in some ciliates. Single-strand $TG_{1-3}$ tails ≧30 bases are present on yeast telomeres at the end of S-phase, and these tails support telomere-telomere interactions, at least in vitro (Wellinger et al., *Cell*, 72:51, 1993). In addition to the telomeric $C_{1-3}A/TG_{1-3}$ sequences, many yeast chromosomes also have sub-telomeric middle repetitive elements called X and Y' that are interspersed with 80–130 bp of $C_{1-3}A/TG_{1-3}$.

Since replication of linear chromosomes by conventional DNA polymerases would result in the progressive loss of DNA from their ends, telomeres are thought to require a specialized mechanism of replication (Watson, *Nature* 239:197, 1972). In several ciliates, and in human and mouse cells, the telomere-specific reverse transcriptase, telomerase, has been detected that adds telomeric repeats onto the ends of G-strand single-stranded telomeric substrates. Although the Tetrahymens telomerase is highly processive in vitro, typically synthesizing about 500 bases (Greider, Mol. Cell Biol. 11:4572, 1991), its processivity appears to be much lower in vivo (Yu and Blackburn, Cell, 67:823, 1991).

All telomerases have an essential RNA component that serves as the template for the addition of telomeric repeats. The substrate requirements for telomere formation in yeast in vivo (Murray and Szostak, *Nature* 305:189, 1983; Pluta et al., *Proc. Natl. Acad. Sci.* 81:1475, 1984) are similar to those for telomerase activity in vitro (Greider and Blackburn, *Cell* 43:405, 1985). In yeast, non-reciprocal recombination resulting in a net increase in telomeric DNA has been detected between plasmid-born telomeric tracts, a process that might also contribute to telomere replication (Pluta and Zakian, *Nature* 337:429, 1989; Wang and Zakian, *Nature* 345: 456, 1990). To at least some extent, the cellular machinery that replicates telomeres must be conserved among organisms with different telomeric sequences. Telomeric DNA from several organisms, including Oxytricha, can serve as substrates in yeast for the addition of yeast telomeric repeats (Pluta et al., 1984, supra) and the Tetrahymena telomerase can utilize different telomeric sequences as substrates for elongation (Greider and Blackburn, *Cell* 51:887, 1987).

Telomeric regions have additional properties that distinguish them from other regions of the genome. Genes that are near yeast telomeres are subject to telomeric position effect repression, which reversibly eliminates constitutive transcription, but does not affect induced transcription (Gottschling et al., *Cell*, 63:751, 1990). Yeast telomeric DNA is organized into a non-nucleosomal chromatin structure called the telosome (Wright et al., *Genes & Dev.*, 6:1987, 1992). Telomeres of different chromosomes can be found associated with each other, with the nuclear envelope (Klein et al., *J. Cell Biol.* 117:935, 1992), and with the nuclear scaffold (de Lange, *EMBO J.* 11:717, 1992).

A number of yeast mutations have been found that affect telomeres. The Rap1 protein (Rap1p) has been shown to bind to telomeric sequences in vitro and in vivo (Buchman et al., *Mol. Cell Biol.* 8:5086–99, 1988; Longtine et al., *Curt. Genet.* 16:225, 1989; Conrad et al., *Cell*, 63:739, 1990; Klein et al., 1992, supra; Wright et al., 1992, supra). Some mutations in the essential RAP1 gene cause telomere shortening, while mutations or high levels of expression of the non-DNA binding carboxyl terminus of Rap1p cause telomere lengthening (Conrad et al., 1990, supra; Lustig et al., *Science* 250:549, 1990; Sussel and Shore, *Proc. Natl. Acad. Sci.* 88:7749, 1991; Kyrion et al., *Mol. Cell. Biol.* 12:5159, 1992). Mutations in the gene encoding Rif1p, which interacts with the carboxyl terminus of Rap1p in vivo, also cause telomere lengthening (Hardy et al., *Genes & Dev.*, 6:801–14, 1992). Some mutations in CDC17, the catalytic subunit of DNA polymerase I, cause progressive telomere lengthening (Carson and Hartwell, *Cell*, 42:249, 1985), whereas mutations in the EST1, TEL1 and TEL2 genes cause telomere shortening (Lustig and Petes, *Proc. Natl. Acad. Sci.* 83:1398, 1986; Lundblad and Szostak, *Cell*, 57:633–43, 1989).

Schulz and Zakian, FASEB, Jul. 5, 1992 (not prior art to the present invention) at a yeast chromosomal structural meeting, presented an abstract which indicated that the PIF-1 helicase may be necessary for maintaining proper telomere length and stability.

SUMMARY OF THE INVENTION

A genetic screen to detect yeast mutants that frequently lost expression of sub-telomeric genes identified two mutations in a single complementation group. The gene affected by the mutations was cloned and found to be identical to PIF-1. Pif1p (the protein encoded by PIF-1) is a 5' to 3' DNA helicase that is said to affect mitochondrial recombination and maintenance. The telomeric phenotypes of PIF-1 mutants were not a result of respiratory deficiency since mutations in different PIF-1 AUG codons separated the mitochondrial and nuclear phenotypes. The increased loss of expression of sub-telomeric genes on a YAC or on chromosome VII seen in pi11 mutants was due to deletion of the subtelomeric region of the chromosome and the generation of a new telomere at proximal sites. In pif1 mutants, de novo telomere formation usually occurred at sites with little or no homology to telomeric DNA. Mutations in PIF-1 also caused all telomeres to become longer. These results indicate that the Pif1 helicase is an inhibitor of both de novo telomere formation, and telomere elongation.

Applicant has thus identified a specific helicase in a eucaryotic cell responsible for altering the viability of that cell. The helicase appears to work by controlling the activity of telomerase or other replication-related biomolecules within a cell, and thus affects the ability of a higher eucaryotic cell to divide for any given number of generations. That is, the helicase is related to cell senescence. While the helicase has been identified in the yeast Saccharomyces, those of ordinary skill in the art will recognize that equivalent helicases can be readily identified in other eucaryotes, including other yeasts and humans.

This invention relates to modulating the activity of such PIF-1-type helicases in a manner which either increases or decreases cell senescence, i.e., the viability of such eucaryotic cells. That is, by increasing the activity of the helicase, the level of telomerase activity will be reduced such that the viability of the cell is reduced. In addition, by decreasing the helicase activity within a cell, the activity of the telomerase will be increased, and thus the viability of a cell increased.

Thus, in a first aspect the invention features a method for affecting the viability of a eucaryotic cell by contacting that cell with a modulator of the activity of a PIF-1-type helicase in the cell. Such contacting specifically increases or decreases the specific activity of the helicase in that cell, and thereby the viability of the cell. Preferably, such modulators are specific inhibitors of PIF-1-type helicases, and do not modulate other helicases, or other enzymes within a cell. Thus, they are preferably distinct from anthracycline antibiotics. Bachar et al., 41 *Mol. Pharm.* 993, 1992.

As discussed above, by viability is meant the ability of a cell to divide. Modulators of the activity of a PIF-1-type helicase will either increase or decrease the number of cell divisions through which that cell may pass. Such numbers are readily measured by methods well known to those in the art.

By modulator is simply meant an agent such as an oligonucleotide or small molecule (less than about 5000 molecular weight) which is able to specifically interact with the PIF-1-type helicase, with DNA or RNA encoding that helicase, with naturally occurring inhibitors or activators of the helicase, or with DNA or RNA encoding that helicase. Such modulators will increase the specific activity of the helicase in the cell, either by directly interacting with the helicase as an activator or inhibitor, by indirectly acting at the DNA or RNA level to reduce or increase production of helicase protein, or at the level of other proteins which interact with the helicase or with a nucleic acid encoding the helicase.

By PIF-1-type helicase is meant to include those helicases which have an activity essentially as described for the PIF-1 helicase of Saccharomyces described herein. It is also meant to include analogous proteins in yeasts and humans which can be identified by standard hybridization procedures using the Saccharomyces PIF-1-encoding nucleic acid as a probe. Such hybridization may be performed under non-stringent hybridization conditions and clones encoding DNA or RNA identified in this manner can be readily screened (using methods described herein or referred to in the art cited herein) to determine whether they have the desired helicase activity. PCR and use of complementation of a yeast mutation by a human gene can also be used to clone the human homolog.

In addition, modulators of the activity of PIF- 1-type helicases in Saccharomyces or other yeasts can be used in humans directly, or as lead compounds in the design of other modulators suitable for use in humans. Such modulators may be targeted to a specific cell if this is desirable using techniques well known to those of ordinary skill in the art.

In a second aspect, the invention features a method for treatment of a disease or condition in a patient by identifying a patient suffering from a disease or condition caused by a high or low level of telomerase activity in a cell, and contacting that cell in the patient with a modulator as described above.

Such diseases or conditions include cancer and fungal infections, such as infection with Candida. Such diseases caused by an increased level of telomerase activity include cancer, in which immortalized cancer cells have high telomerase activity which can be modulated by a method of the present invention. That is, by increasing the activity of the helicase, the level of the telomerase activity may be reduced, and thus the viability of the cancer cell (i.e., the number of cell divisions which it can pass through) is reduced. Conditions exemplified by an increased level of telomerase activity include fungal infections in which the fungal cells have higher levels of telomerase activity than the surrounding host (e.g., human) cells, which can again be modulated as described above using helicase activators.

Diseases or conditions caused by a low level of telomerase activity include those in which the viability of a cell may be increased by increasing telomerase activity. This can be achieved by reducing helicase activity in those cells using modulators as described above. Such diseases or conditions include old cells within an individual patient which have become limiting in that patient. For example, vascular cells, immune cells, skin cells, and heart cells, muscle cells and the like. Thus, increased vitality of such cells may be achieved by contacting those cells with a modulator of helicase which decreases the helicase activity within that cell, and thereby increases residual telomerase activity or otherwise activates telomerase, and thus the number of cell divisions through which that cell may pass prior to death. Those in the art will recognize that many diseases associated with old age, or premature aging in certain individuals, can be treated in this manner.

In a third aspect, the invention features a method for identifying a modulator of a PIF-1-type helicase by contacting a potential modulator with such a helicase and assaying the activity of the helicase in vitro or in vivo. Useful modulators in this invention are those which specifically increase or decrease the activity of the helicase, or can be modified to be specifically targeted to a target cell in need of helicase modulation. The invention also features unique modulators identified by this method by unique is simply meant compounds which were not known prior to their identification as useful modulators of this invention, or as potential modulators of this invention.

Other features and advantages of the invention will be apparent from the following description of the preferred embodiments thereof, and from the claims.

DESCRIPTION OF THE PREFERRED EMBODIMENTS

BRIEF DESCRIPTION OF THE DRAWINGS

FIG. 2 shows telomeres of wild-type, tst1-1 and pif1D strains. Specifically.

FIG. 3 shows the effects of PIF-1 AUG mutations on petite formation, Leu⁺, FOAR colony formation and telomere length. Specifically.

FIG. 4 shows the structure of FOAR YACs from wild type and PIF-1 mutant strains. Specifically, FIG. 4B shows quantitation of different classes of $Leu^+$ FOAR events For each PIF-1 genotype, the percent of $Leu^+$, FOA resistance resulting from deletions larger than 4.7 kbp, deletion of 4.7 kbp with telomere formation at the internal tract of $C_4A4/T4G4$, and URA3 point mutation is shown. The rates of each class was determined by multiplying the rate of total $Leu^+$, FOA resistance by the fraction of each class;

FIG. 5 shows the effects of a PIF-1 mutation on chromosome loss, gene conversion and reciprocal recombination. The two copies of chromosome VII that are present in the ade2 disome strain are shown, as well as the results of loss or recombination of chromosome VII. The reciprocal recombination must be followed by homozygosis to yield the product shown. The rates (x $10^{-5}$) of different events in wild type and pif1-m2 cells are shown below; and FIG. 6 shows long telomeres associated with a RIF1 deletion do not affect telomere stability Specifically, FIG. 6B shows the effects of RIF1 deletion on generation of $Leu^+$, FOAR cells. Rates of Leu+, $FOA^R$ colony formation of cells carrying YAC-VS5 (x $10^{-6}$) are shown below the genotype.

MODULATORS

Figure 1:
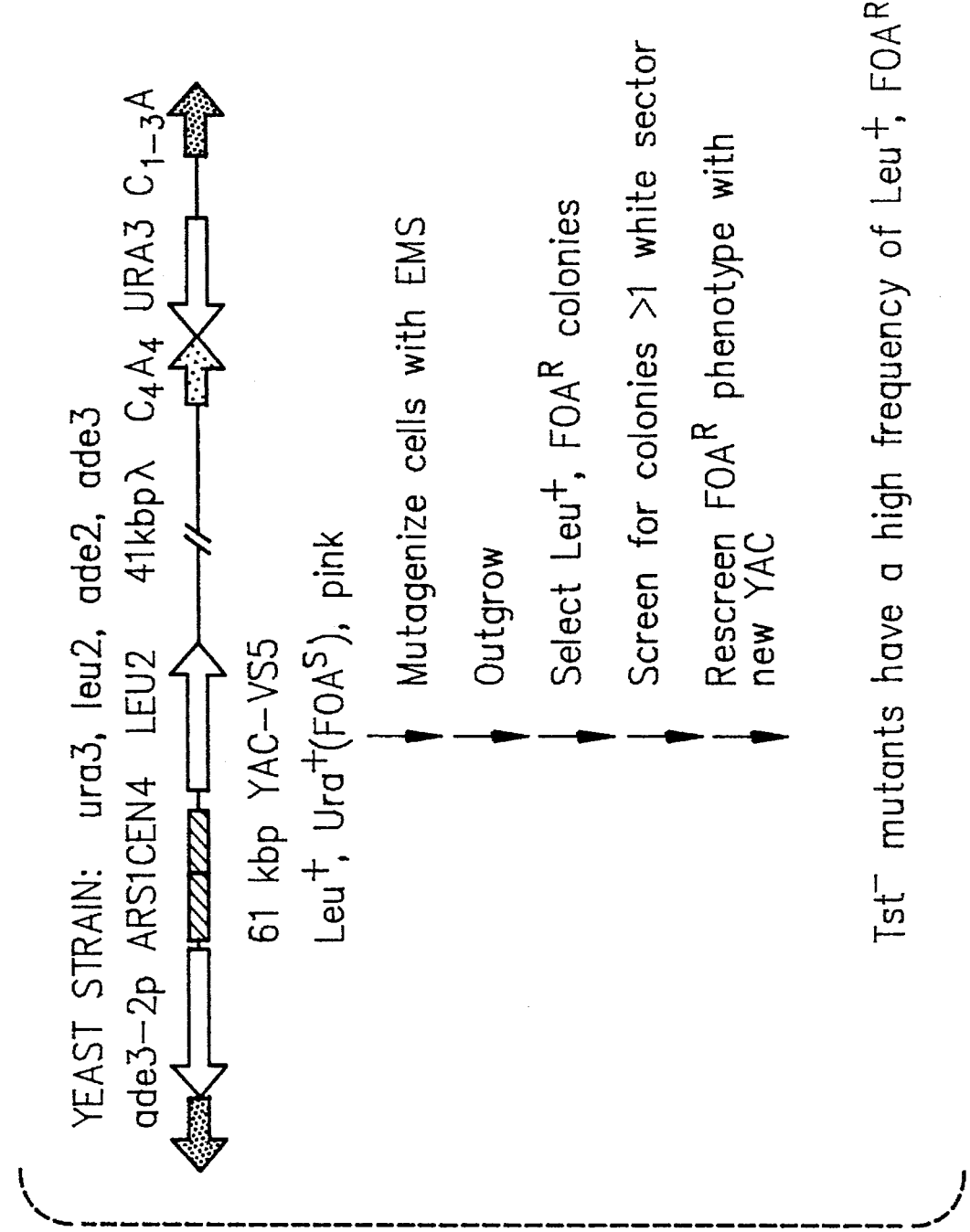
FIG. 1 shows a system used to isolate TST mutants. Only genetic markers that are relevant to the isolation of mutants are noted. YAC-VS5 is not drawn to scale.

Modulators of the present invention can be identified as described above. Generally, any specific helicase assay can be used to identify such modulators, for example, as described by Lahaye et al., The *EMBO Journal,* 10:997, 1991, or as described herein, by use of oligonucleotides which are able to base pair with nucleic acid encoding a desired helicase.

Those in the art will recognize that antisense molecules, decoy molecules or ribozymes can be used as modulators of helicase activity in vitro. Such modulators can be administered using standard procedures well known to those of ordinary skill in the art. Small molecule modulators can also be readily identified by screening naturally product libraries or combinatorial libraries, for example, for peptides which are able to interact with the helicase or proteins associated with the helicase to increase or decrease the activity of that helicase. Such molecules can again be administered using standard procedures, examples of which now follow.

ADMINISTRATION

Selected modulators or agents, e.g., small molecules, oligonucleotides or ribozymes can be administered prophylactically, or to patients suffering from a target disease, e.g., by exogenous delivery of the agent to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of oligonucleotides are also suitable.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery, e.g., for oligonucleotides, that may be used include:

a. encapsulation in liposomes, b. transduction by retroviral vectors, c. conjugation with cholesterol, d. localization to nuclear compartment utilizing antigen binding site found on most snRNAs, e. neutralization of charge of oligonucleotides by using nucleotide derivatives, and f. use of blood stem cells to distribute oligonucleotides throughout the body.

At least three types of delivery strategies are useful in the present invention, including: agent modifications, particle carrier drug delivery vehicles, and retroviral expression vectors. Unmodified agents may be taken up by cells, albeit slowly. To enhance cellular uptake, the agent may be modified essentially at random, in ways which reduce its charge but maintain specific functional groups. This results in a molecule which is able to diffuse across the cell membrane, thus removing the permeability barrier.

Modification of agents to reduce charge is just one approach to enhance the cellular uptake of these larger molecules. The structural requirements necessary to maintain agent activity are well understood by those in the art. These requirements are taken into consideration when designing modifications to enhance cellular delivery. The modifications are also designed to reduce susceptibility to enzymatic degradation. Both of these characteristics should greatly improve the efficacy of the agent.

Chemical modifications of the phosphate backbone of oligonucleotides will reduce the negative charge allowing free diffusion across the membrane. This principle has been successfully demonstrated for antisense DNA technology. In the body, maintenance of an external concentration will be necessary to drive the diffusion of the modified oligonucleotides into the cells of the tissue. Administration routes which allow the diseased tissue to be exposed to a transient high concentration of the agent, which is slowly dissipated by systemic adsorption are preferred. Intravenous administration with a drug carrier designed to increase the circulation half-life of the oligonucleotides can be used. The size and composition of the drug carrier restricts rapid clearance from the blood stream. The carrier, made to accumulate at the site of infection, can protect the oligonucleotides from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver agents to cells and that the agent remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents and protein-based pharmaceuticals.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the infected cells. Chemical modification of the agent to neutralize negative or positive charges may be all that is required for penetration. However, in the event that charge neutralization is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the targeted cell, or the liposome phospholipids can participate directly with the modified agent and permeability enhancer in facilitating cellular delivery. In some cases, both the agent and permeability enhancer can be formulated into a suppository formulation for slow release.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the agent to an accessible diseased or other tissue. Subcutaneous administration drains into a localized lymph node which proceeds through the lymphatic network into the circulation. The rate of entry into the circulation has been shown to be a function of molecular weight or size. The use of a liposome or other drug carrier localizes the agent at the lymph node. The agent can be modified to diffuse into the cell, or the liposome can directly participate in the delivery of either the unmodified or modified agent to the cell.

Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 10–2000 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of agent within the target cell is dependent upon the rate of uptake and degradation. Decreasing the degree of degradation will prolong the intracellular half-life of the agent. Thus, chemically modified agents, e.g., oligonucleotides with modification of the phosphate backbone, or capping of the 5' and 3' ends of the oligonucleotides with nucleotide analogues may require different dosaging.

Such modulators can be used as described herein to modulate helicase activity in vivo or in vitro and thus modulate telomerase activity. Such modulation can be monitored by assaying telomere length and telomerase activity.

PIF-1-TYPE HELICASE

Applicant devised a genetic screen that allowed the isolation of mutations that increase the frequency of loss of sub-telomeric gene expression, or that affect the replication, transcription, chromatin structure or nuclear localization of telomeric regions. Two mutations were found that increased the loss of subtelomeric genes, but not genes located internally. These mutations also caused telomeres to become longer and more heterogeneous. The gene affected by the mutations was cloned and found to be identical to PIF-1 (petite integration frequency).

PIF-1 is required for the recombination that is frequently seen between rho$^+$ and tandemly arrayed rho mitochondrial DNA genomes (Foury and Kolodynski, *Proc. Natl. Acad. Sci.* 80:5345, 1983). It is also required for maintenance of mitochondrial DNA, especially at high temperatures, and for repair of mitochondrial DNA treated with UV light or ethidium bromide. Pif1p appears to recognize an unusual DNA topology, since only mitochondrial genomes that contain A-T rich palindromes show increased PIF-1 dependent recombination (Foury and van Dyck, *EMBO J.* 4:3525, 1985). Pif1p is a 5' to 3' DNA helicase (Lahaye et al., *EMBO J.* 10:997, 1991). Previous work suggested that Pif1p functions only in mitochondria. Here, we show that Pif1p also affects telomere length and the frequency of de novo telomere formation.

Figure 3A:
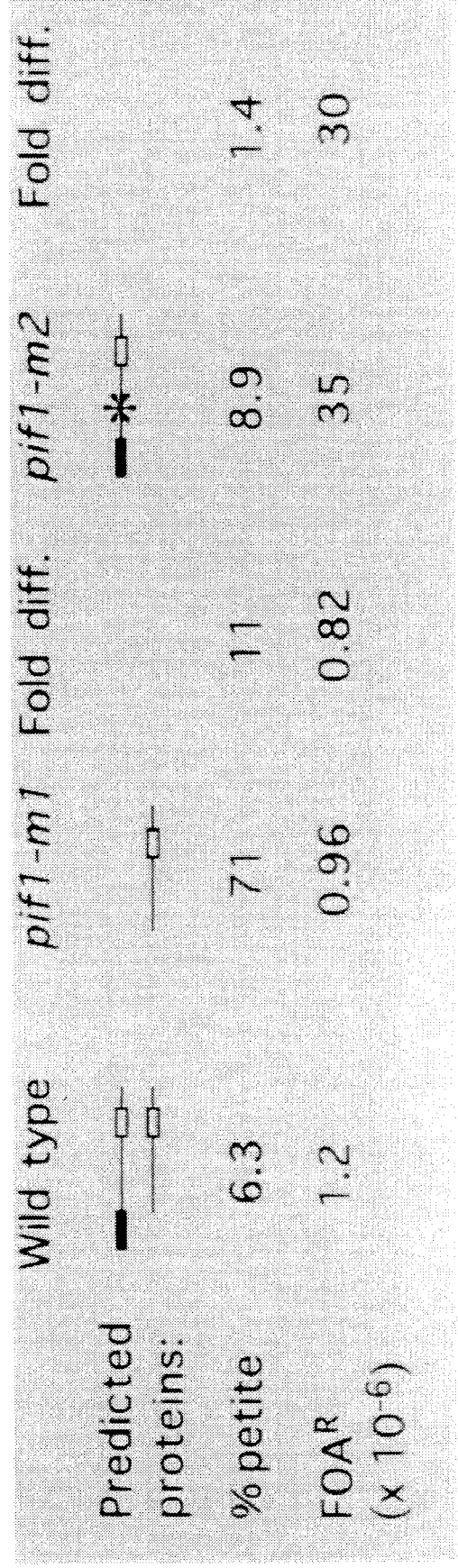
FIG. 3A shows quantitation of petite and Leu⁺, FOAR colony formation. Black and white bars represent putative mitochondrial and nuclear protein targeting sequences respectively. Asterisk represents methionine to alanine change in protein. Sequences are not drawn to scale. % petite is the fraction of cells in a colony that are petite. $FOA^R$ is the rate of generation of FOA resistance of cells bearing YAC-VS5. Fold diff. is the fold difference from wild type.
Figure 3B:
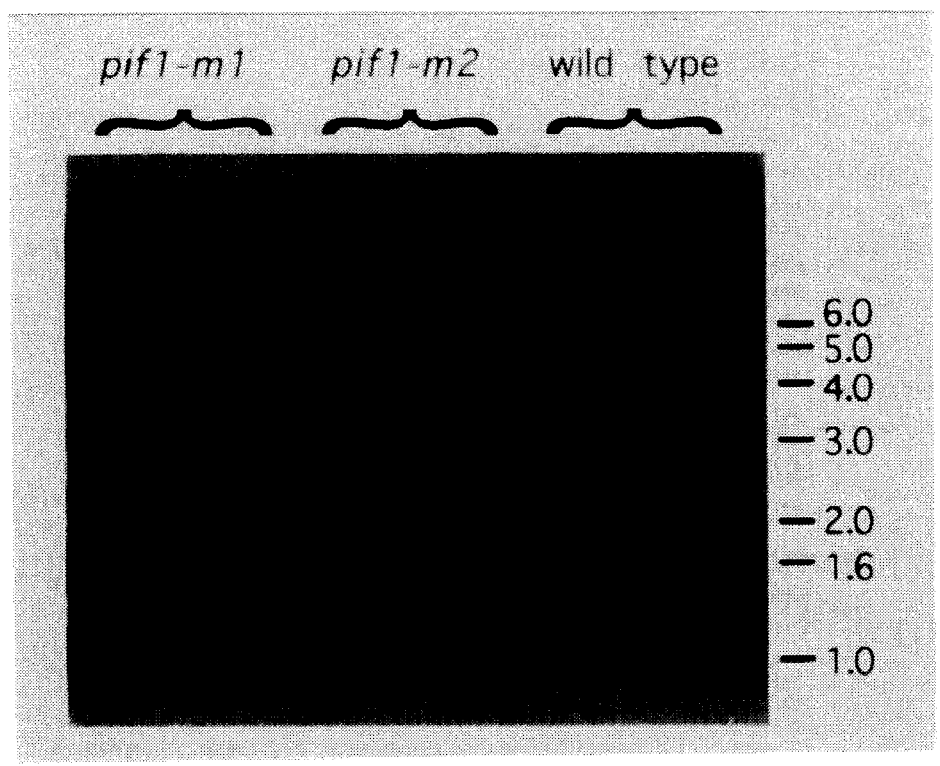
FIG. 3B shows telomeres of wild-type, pif1-m1 and pif1-m2 strains. DNA was isolated from 4 separate cultures of each strain, cut with XhoI, run on a 1% agarose gel and analyzed by Southern blotting. The blot was hybridized with a $C_{1-3}A$ probe.

By screening for mutations that increased the loss of expression of sub-telomeric genes, we identified two mutations in the nuclear gene PIF-1. The PIF-1 gene encodes a 5' to 3' DNA helicase that was previously thought to affect only mitochondrial DNA recombination and maintenance (Lahaye et al., *EMBO J.* 10:997, 1991). The effects of Pif1p on mitochondria and telomeres can be separated by mutation (FIG. 3). Mutation of the first AUG codon of the PIF-1 open reading frame caused mitochondria to be unstable, but telomeres were unaffected. Conversely, mutation of the second AUG codon affected telomeres, but not mitochondria (FIG. 3). These results indicate that sub-cellular localization of Pif1p is determined by initiation codon usage and demonstrate that the effects of pif1 mutations on telomeres are not a secondary consequence of a respiratory deficient phenotype. Thus, our experiments define a new role for the PIF-1 gene in telomere function.

Figure 2A:
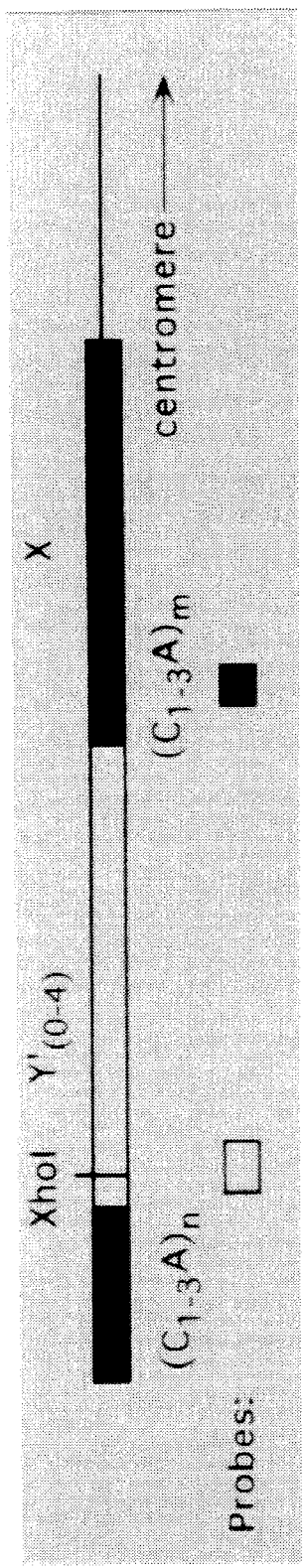
FIG. 2A is a schematic diagram of a yeast telomere and the position of telomeric probes is indicated. X and Y' are sub-telomeric elements found at all or most telomeres.
Figure 2B:
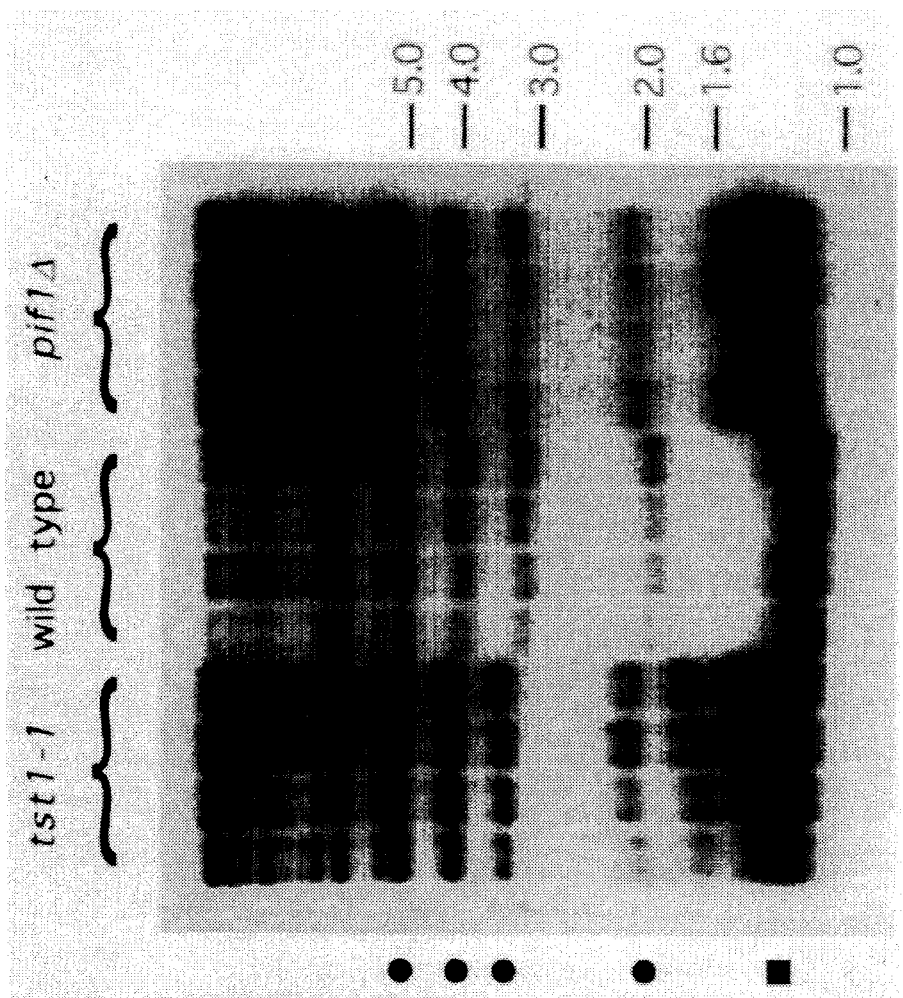
FIG. 2B shows DNA isolated from 4 separate cultures for each strain, digested with XhoI, run on a 1% agarose gel and analyzed by Southern blotting. The blot was hybridized with a Y' KpnI fragment probe.
Figure 4A:
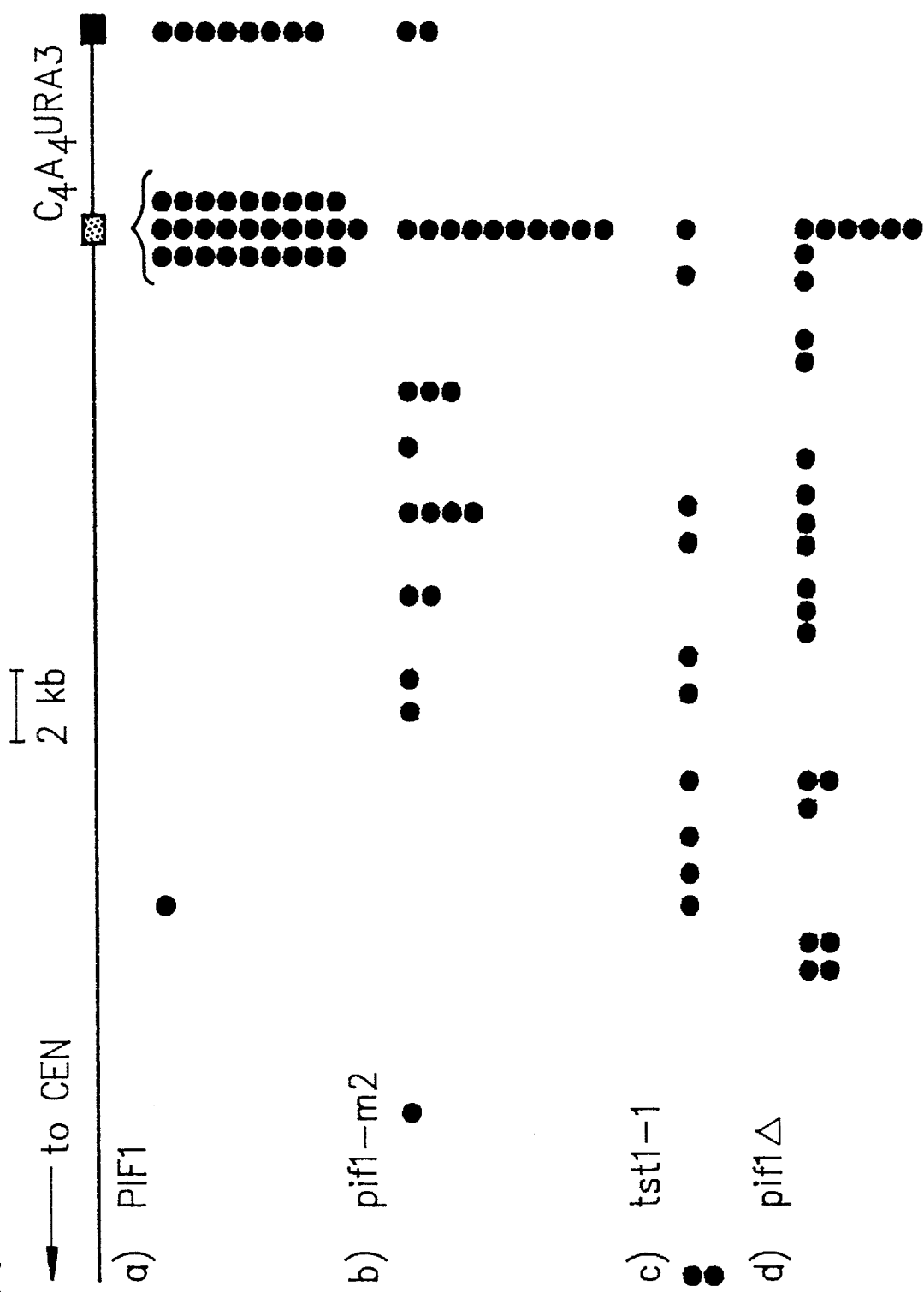
FIG. 4A shows the arm of YAC-VS5 that contains URA3 (above). The black box at right indicates the telomere, and the shaded box indicates the internal tract of $C_4A4/T4G4$. Dots indicate the position of the new end of individual YAC's from different $Leu^+$, FOAR cultures.

Loss of function mutations in the PIF-1 gene affected telomeres in three ways. First, they caused an increase in the length and heterogeneity of telomeres (FIG. 2 and 3). This increase is specific for terminal $C_{1-3}A$ tracts since the lengths of internal tracts of $C_{1-3}A$ were unaltered in pif1-m2 cells (data not shown). Second, they caused physical loss of sub-telomeric genes both on YAC-VS5 (Table 1, FIG. 4) and on chromosome VII (Table 2): terminal deletions of YAC-VS5 were recovered at rates $\sim 10^3$ to $\sim 10^4$ times higher in pif1 cells than in wild type cells (FIG. 4). Third, mutations in PIF-1 resulted in an altered specificity of telomere formation. In wild type cells, the formation of new telomeres on YAC-VS5 occurred at the $C_4A_4/T_4G_4$ tract proximal to the URA3 gene (FIG. 4). In contrast, in pif1 cells most new telomeres were added at different places within phage DNA that have little or no homology to telomeric sequences.

TABLE 1

The effect of the tst1-1 and pif1Δ mutations on the rate of generation of Leu⁺, FOA resistance and percent petite colony formation for cells carrying YAC-VS5. Results of 3 different assays in the parental wild type strain are shown for Leu⁺, FOA resistance.

| | $FOA^R$ ($\times 10^{-6}$) | Fold diff. | % petites | Fold diff. |
|---|---|---|---|---|
| wild type | 0.87, 1.0, 1.6 | (1) | 6.3 | (1) |
| tst1-1 | 170 | 146 | 77 | 12 |
| pif1Δ | 600 | 522 | 93 | 15 |

TABLE 2

The effect of the pif1-m2 mutation on the rate of generation of FOA resistance when the URA3 gene is located at different genomic environments. Multiple values represent independent experiments.

| | $FOA^R$ Rate ($\times 10^{-7}$) PIF1 genotype | | |
|---|---|---|---|
| URA3 location: | wild type | pif1-m2 | fold difference |
| V internal | 0.92 | 1.1 | 1.2 |
| VII-L telomere | 0.76, 1.2, 1.6 | 5.8, 8.1, 10 | 6.6 |
| YAC telomere | 8.7, 10, 16 | 350 | 30 |

The increased recovery of terminal deletions in pif1 cells could have been caused by an increase in DNA lesions throughout the genome. DNA lesions such as single and double-strand breaks are known to cause an increase in chromosome loss and recombination in yeast (Mortimer et al., *Proc. Natl. Acad. Sci.* 78:5778, 1981; Hartwell and Smith, *Genetics* 110:381, 1985; Strathern et al., *Genetics* 127:61, 1991). However, pif1-m2 cells displayed wild type levels of chromosome loss, reciprocal recombination, gene conversion (FIG. 5), and UV sensitivity (data not shown). In addition, the rate of recombination between internal $C_{1-3}A$ tracts was not affected in pif1 cells (data not shown). Since the $FOA^R$ cells generated in pif1 cells have lost the URA3 gene, the pif1 phenotype does not result from an extension of telomere position effect to more proximal regions of the chromosome.

Mutations in PIF-1 could increase the number of terminal deletions either by increasing the number of telomere loss events, or by increasing the healing of chromosomes that have spontaneously lost a telomere. The fact that telomeres are longer in pif1 mutants argues against the first possibility. A rif1Δ strain had telomeres even longer than those in pif1 cells, yet did not show more terminal deletions, demonstrating that long telomeres are not by themselves sufficient to cause an increase in terminal deletions (FIG. 6). Moreover, it is difficult to explain how a mutation that causes reduced telomere function could also allow increased addition of telomeres onto non-telomeric DNA. Therefore, the most likely explanation for the increased recovery of terminal deletions in pif1 cells is that healing of broken chromosomes by de novo telomere formation occurs at an increased rate. This increase was due to an increase in telomere formation both at the internal $C_4A_4/T_4G_4$ telomeric tract and at sites that have little sequence similarity to telomeric DNA (FIG. 4).

Telomere length regulation in yeast is complex, involving many gene products (see introduction), and it is thought to involve a balance between elongation and shortening. The phenotype of pif1 cells suggest that Pif1p inhibits telomere elongation and de novo telomere formation. Pif1p could keep telomeres short by reducing replication or by enhancing degradation. There is evidence in yeast for at least two proteins whose presence at telomeres seems to protect telomeres from replication (Runge and Zakian, *Mol. Cell. Biol.*, 11:2919, 1989; Conrad et al., *Cell*, 63:739, 1990; Hardy et al., *Genes & Dev.* 6:801, 1992, Wiley and Zakian, in prep.). One of these proteins is Rif1p (Hardy et al., 1992, supra). The effects of mutations in PIF-1 and RIF1 on telomere length (FIG. 6) or of mutations in PIF-1 and expression of the carboxy terminus of Rap1p on telomere length were additive (data not shown). Therefore, Pif1p affects telomere length via a different pathway than that affected by removal of these proteins.

Since Pif1p is a 5' to 3' DNA helicase in vitro (Lahaye et al., 1991, supra) and the helicase motifs extend throughout much of the protein (Foury and Lahaye, *EMBO J.* 6:1441, 1987), it is tempting to speculate that Pif1p exerts its effects at telomeres by acting as a helicase. Since PIF-1 can be deleted without compromising viability, its helicase activity is either non-essential or partially redundant with another yeast DNA helicase such as RAD3 (Sung et al., *Proc. Natl. Acad. Sci.* 84:6045, 1987), RAD5 (Johnson et al., *Mol. Cell. Biol.* 12:3807, 1992), RAD16 (Dang et al., *Nuc. Acids Res.* 20:3925, 1992), HPR5 (Rong and Klein, *J. Bact. Chem.*, 1252, 1993), or CHL1 (Gerring et al., *EMBO J.* 9:4347, 1990). How might a helicase decrease telomere length and telomere formation? One possibility is that the Pif1 helicase unwinds chromosomes from their ends thereby making them susceptible to single strand specific nucleases. However, the Pif1 helicase requires a 5' single strand tail to initiate unwinding (Lahaye et al., 1991, supra), and 5' tails have not been detected on yeast telomeres at any point in the cell cycle (Wellinger et al., *Cell*, 72:51, 1993). Moreover, it is difficult to explain the increase in de novo telomere formation or the altered specificity of telomere formation by this model.

The Pif1p helicase has the right polarity to sit on the lagging strand and unwind the double helix ahead of the replication fork. If the Pif1p helicase serves this function, it probably does so only in telomere proximal regions, since pif1 cells have wild type levels of chromosome loss and recombination. In this model, we imagine that in pif1 cells conventional replication forks stall as they near the telomere. The acquisition of single-strand $TG_{1-3}$ tails, the predicted intermediate in telomere replication by either a telomerase or a gene conversion model of telomere replication, is temporally coupled to conventional replication of sub-telomeric DNA (Wellinger et al., 1993, in press). Stalling of the replication fork as it approached the end of the chromosome might allow more time for the synthesis of $TG_{1-3}$-tails, thereby explaining the increase in telomere length associated with PIF-1 mutations. However, this model does not provide a ready explanation for the altered specificity characteristic of de novo telomere formation in pif1 cells.

The model that most simply explains the phenotypes of PIF-1 mutants is that Pif1p acts as a telomeric DNA/ telomerase RNA helicase. According to this model, Pif1p keeps telomeres short and prevents telomere addition onto broken ends by dissociating telomerase from its substrate. In the absence of Pif1p, telomerase could add telomeric repeats onto sequences that have little or no telomere homology. Developmental regulation of a Pif1p-like activity might explain the addition of telomeric sequences by telomerase onto nontelomeric substrates during macronuclear development in Tetrahymena. Changes in a Pif1p-like activity could also be responsible for the differences in telomerase activity seen in normal and tumorigenic cells. Since several helicases are structurally and functionally conserved between yeast and humans (Friedberg, 1992), it will be possible to identify a human homolog of PIF-1. Given the above model, Pif1p and its human homolog will reduce the processivity of human telomerase in vitro.

METHODS

The following materials and methods were used in examples described below. These methods and examples are not limiting in the present invention; those of ordinary skill in the art will recognize that many equivalent methods and examples can be used.

While specific details are provided herein of certain nucleic acids used in the examples, such nucleic acids are not essential for practice of the invention, and can be readily substituted by equivalent nucleic acids well known for those in the art.

GENERAL PROCEDURES

DNA manipulations were performed as described (Sambrook et al., Molecular Cloning, A Laboratory Manual, Second Edition (Cold Spring Harbor) N.Y.: Cold Spring Harbor Press, 1989). To convert fragments with overhangs to blunt-ended fragments, the Klenow fragment of DNA polymerase was used for filling in 5' overhangs and T4 DNA polymerase was used to trim 3' overhangs. Yeast media and growth conditions were as described (Zakian and Scott, 1982, supra; Runge and Zakian, *Mol. Cell Biol.* 9:1488, 1989).

YEAST STRAIN CONSTRUCTION

The yeast strain VPS105 was used for all of the experiments in this paper except where noted. VPS105 was a derivative of the chromosome VII disomic strain DDM30 (Runge et al., *Mol. Cell Biol.* 11:2919, 1991). Haploid, white (ade3) segregants of DDM30 were isolated to yield strain VPS100 (MATα ade2 ade3 leu2-3,112 ura3Δ trp1Δ aro2 can1). VPS100 was crossed to YNN214 (MATa ura3-52 lys2-801 ade2-101) (Sikorski and Hieter, *Genetics* 122:19, 1989). The resulting diploid was sporulated and a spore product of genotype MATa ade2 ade3 leu2-3,112 ura3Δ can1 lys2-801 was backcrossed again to VPS100 to yield VPS105 (MATα ade2 ade3 leu2-3,112 ura3Δ trp1Δ lys2-801 can1). The mating type of VPS105 was switched to yield VPS106 by using the pGAL-HO plasmid as described (Herskowitz and Jensen, *Meth. Enz.* 194:132, 1991). VPS105 was mated with VPS106 to yield VPS107. The RIF1 gene, obtained from David Shore, was disrupted by transforming VPS105 and VPS105 pif1 -m2 with pCH450RT (the plasmid used is not critical, many other plasmids can be used to disrupt this gene), resulting in deletion of 3.6 kbp of RIF1 and insertion of 1.7 kbp of TRP1.

Three derivatives of VPS105 were made to test the effects of PIF-1 mutations on the URA3 gene located at different places in the genome. The deletion of the URA3 gene on chromosome V was reverted to wild type by transformation with the HindIII URA3 fragment of YEP24 (Rose et al., 1987). The yeast transformation procedure used was as described (Hill et al., *Nuc. Acids Res.* 19:5791, 1991) except that single stranded carrier DNA was added (Schiestl and Gietz, *Curr. Genet.* 16:339, 1989). The URA3 gene was placed directly at the telomere of chromosome VII-L in strain VPS105 by transformation with an EcoRI-SalI fragment from padh4::URA3 -TEL (Gottschling et al., *Cell,* 63:751, 1990). A similar integrant in strain YPH499 (MATa ura3-52 lys2-801 ade2-801 trp1-Δ1 his3-Δ200 leu2-Δ1) (Sikorski and Hieter, 1989, supra) was generously provided by E. Wiley. The URA3 gene was placed 2.6 kbp from the telomere of chromosome VII-L by transformation with a HindIII-EcoRI fragment of pVS21. pVS21 is composed of the EcoRI-SmaI URA3 fragment of pVS20, and the EcoRI-HpaI fragment of pYA4-2 (Walton et al., *Cell,* 46:857, 1986). pVS20 was made by ligating the EcoRI-SalI yeast telomeric fragment of pYTCA-2 (Gottschling et al., 1990, supra) to the EcoRI-SalI URA3 fragment of pVS3.

CONSTRUCTION OF YAC-VS5

The SmaI-EcoRI fragment of M13#17 containing 108 base pairs of Oxytrichia telomeric DNA (Pluta and Zakian, 1989, supra) was blunt-ended and ligated to SmaI cut YCp2La (Wellinger and Zakian, *Proc. Natl. Acad. Sci.,* 86:973, 1989) to yield YCpVS1. YCpVS1 was linearized with SalI, and a 2.6 kbp SalI-XhoI fragment from the Drosophila white gene (obtained from R. Levis) was inserted to yield YCpVS3. YCpVS3 was converted from a circular plasmid to a ~16.5 kb linear plasmid called YLpVS3 in yeast strain VPS105 as described (Wellinger and Zakian, 1989, supra). YLpVS3 was converted into a ~60.6 kb yeast artificial chromosome called YAC-VS5 by integration of a NotI fragment of λVS1. λVS1 is a derivative of λGT2 (Panasenko et al., *Science,* 196:188, 1977) that was made as follows. The HpaII chloramphenicol resistance gene fragment of pACYC184 (Chang and Cohen, *J. Bact.* 134:1141, 1978) was ligated to pUC18 (Sambrook et al., 1989, supra) cut with SmaI to yield pVPS4. pVS4 was cut with SacI and AatII, and the chloramphenicol resistance fragment was ligated to a pUC119 (Sambrook et al., 1989, supra) SacI-AatII fragment to give pVS6. pVS6 was linearized with SacI, blunt-ended and ligated to the blunted SalI-XhoI LEU2 fragment of YCpL2 (Runge et al., *Mol. Cell. Biol.* 6:2919, 1991) to give pVS55. pVS14 was made by ligating the blunted HindIII-HpaI chloramphenicol resistance, LEU2 fragment of pVS55 to ScaI linearized pVS13. pVS13 was made by cutting pVZ1 (Henikoff and Eghtedarzadeh, *Genetics* 117:711, 1987) with HindIII and BamHI, blunting, and recircularizing. λVS1 was created by blunt-ending EcoR1 cut λGT2, and ligating with pVS14 that was cut with XbaI and blunted.

YAC-VS5 was transferred between strains by mating with karyogamy deficient (Kar⁻) strains (Dutcher, *Mol. Cell. Biol.* 1:245, 1981; Wellinger and Zakian, *Proc. Natl. Acad. Sci.* 86:973, 1989). The Kar⁻ strains used were 213 cir° (MATa kar1-1 leu2-3,112 ura3-52 his7 $CYH2^R$) 212 cir° (MATs kar1-1 leu2-3,112 ura3-52 his7 $CYH2^R$ ade1) (Runge and Zakian, *Mol. Cell Biol.* 9:1488, 1989) and 6-3$CYH^R$ (MATα kar1-1 trp1Δ leu2-3,112 his ura3 $CYH2^R$), which is a spontaneous cycloheximide resistant derivative of 6-3 (Wellinger and Zakian, 1989, supra).

MUTAGENESIS AND ISOLATION OF MUTANTS

VPS105 cells carrying YAC-VS5 were mutagenized to 50–70% killing with EMS as described (Lawrence, *Meth. Enz.* 194:273, 1991). After mutagenesis, cells were divided into 5 pools with $2.6\times10^6$ viable cells, 25 mls of YC glucose media lacking uracil was added, and the cultures were grown at 30° C. to reach saturation. 25 microliters of cells were subcultured into 25 mls of YC glucose media lacking leucine. The subculturing was repeated three more times to overcome the phenotypic lag seen with some mutations that affect telomeres. After each subculture, an aliquot of cells was plated on media lacking leucine (to select for the YAC) and containing FOA to select for loss of expression of the subtelomeric URA3 gene. The plates also contained 8% glucose and 10 mg/l adenine to enhance the development of red colony color. Cells were plated to yield 200–600 colonies per plate. This procedure was also carried out on VPS106 cells carrying YAC-VS5. Approximately 30,000 $FOA^R$ colonies were screened with a dissecting microscope for pink colonies with one or more white or light pink sectors. 185 candidates were restreaked on media containing leucine. White, Leu⁻ colonies that had lost the YAC were isolated, and a new YAC was reintroduced by Kar⁻ mating. The FOA resistance phenotype of 3 cultures of each candidate was tested. 12 mutants were isolated. Most of the mutants were independent, since they came from different pools. The tst1-1 and tst1-2 mutants were isolated from the second and third subcultures respectively. The tst1-1 mutation was backcrossed twice for the experiments shown herein.

CLONING OF TST1/PIF-1:

VPS105 tst1-1 cells were transformed with a YCp50 yeast DNA library (Rose et al., *Gene* 60:237, 1987). Since wild-type cells grow 1.4 times faster than tst1-1 cells, we enriched for clones that had the TST1 gene by growing pooled cultures of transformants in liquid media. Five independent cultures of transformants were outgrown in YC liquid lacking uracil for about 20 generations (6400 transformants, or about six genome equivalents, were obtained, as determined by plating an aliquot of the transformation before liquid outgrowth). These cultures was subcultured for another 10 generations in YEPD, and plated for single colonies on YC plates lacking uracil. Plasmid DNA was isolated from colonies from different cultures that grew well and transformed into bacteria. Two plasmids that conferred healthy growth when reintroduced into VPS105 tst1-1 yeast were studied further. Restriction fragments from one of the plasmids were subcloned into pRS314 (Sikorski and Hieter, 1989, supra) to test complementation of the tst1-1 mutation. The sequence of 106 bp of a BamHI subfragment that did not complement was determined using a SEQUENASE® kit (United States Biochemical).

We determined that the PIF-1 gene is located about 140 kb from the left telomere of chromosome XIII (near sup5) by hybridizing a SacI-EcoRV PIF-1 probe to a set of filters that contains an ordered λ clone bank of the yeast genome.

OTHER MUTATION SIN THE PIF-1 GENE:

The PIF-1 gene was disrupted by the following procedure. A KpnI-ApaI genomic fragment containing the 3' end of the PIF-1 gene was cloned into KpnI and ApaI cut pRS304, which carries the TRP1 gene (Sikorski and Hieter, 1989, supra). This plasmid was cut with SmaI and SalI, and a DraI-XhoI fragment from the 5' end of PIF-1 was inserted to yield pVS101. pVS101 was cut with ApaI and transformed into diploid VPS107, selecting Trp⁺ colonies. Correct integration deletes 399 bases of PIF-1 (from the DraI site to the KpnI site) and inserts 4.3 kbp of pRS304 into the PIF-1 gene. The PIF-1/pif1 Δ diploid was sporulated, and 5 tetrads were dissected. There was 2:2 cosegregation of the Trp⁺ and unstable mitochondria phenotypes in these tetrads. Analysis of the telomeres of two of the tetrads showed that the Trp⁺ spores had long heterogeneous telomeres.

The first and second AUG's of the PIF-1 open reading frame were changed to alanine codons using oligonucleotide site directed mutagenesis of dut⁻, ung⁻ phagemid DNA (Sambrook et al., 1989, supra). The oligonucleotides used were: m1 5'ATCAATTTTGGGCCCCAAAGTGG (SEQ. ID. NO. 1) and m2 5' TCGTTTTCTGCCTC-GAGTCGTGGT (SEQ. ID. NO. 2). The m1 and m2 mutations create new ApaI and XhoI sites respectively. The template for mutagenesis was composed of a SacI-ApaI genomic PIF-1 fragment inserted into pRS314 also cut with SacI and ApaI. The PIF-1 PvuII fragment was then transferred to pRS306 (Sikorski and Hieter, 1989, supra) cut with PvuII to yield pVS30 (m1) and pVS31 (m2). Mutations were introduced into the yeast genome by cutting pVS30 or pVS31 with HindIII and selecting Ura⁺ transformants. Excision of the plasmid was selected on FOA plates, and $FOA^R$ yeast were analyzed with Southern blots to determine if they had the appropriate restriction enzyme digestion pattern.

DETERMINATION OF FOA RESISTANCE RATES

FOA resistance rates were determined with 10 culture assays using the method of the median (Lea and Coulson, *J. Genet.* 49:264, 1949; Runge et al., *Mol. Cell Biol.* 11:2919, 1991). Standard deviations were determined according to Lea and Coulson, 1949, and were less than 24%. Viable counts were determined by a plating of an appropriate dilution of a pool of the ten cultures. Rates that were greater than $10^{-5}$/cell/generation were determined by suspending an isolated colony in water, and plating an aliquot on FOA plates. Rates that were less than $10^{-5}$ were determined by inoculating an isolated colony into 1 ml of liquid media, growing to saturation, and plating an aliquot on FOA. Only non-petite (>0.5 mm) colonies were counted for both viable and $FOA^R$ cells.

QUANTITATION OF PETITE COLONIES

Wild type or mutant strains were streaked on synthetic complete media with glucose, and grown for 3 days at 30° C. Colonies from each strain were resuspended in water, aliquots were plated on YEPD plates, and grown for 3 days at 30° C. Colonies smaller than 0.5 mm were scored as petite. Small colonies were replica plated to glycerol medium to verify that they were respiratory deficient. The average frequency of petites in 3 colonies from each strain is reported.

ANALYSIS OF YACs from FOA$^R$ CELLS

Yeast DNA from independent FOA$^R$ Leu$^+$ cells was digested with BstEII and analyzed by Southern blotting. Blots were probed with pVZ1, λ and URA3 random-primed probes (Sambrook et al., 1989). The maximum error in assigning the site of new telomere addition is about 1 kb.

QUANTITATION OF POSITION EFFECT REPRESSION

Wild type or pif1-m2 strains with the URA3 gene directly at the telomere of chromosome VII-L were streaked on YEPD plates and grown for two days at 30° C. Colonies were resuspended in water, and aliquots were plated on synthetic complete plates or FOA plates. The frequency of position effect repression reported is the average frequency of FOA$^R$ cells from 3 colonies of each strain. The standard deviation for these assays was less than 37%. All of the FOA$^R$ colonies were able to grow on media lacking uracil after replica plating.

CHROMOSOME LOSS ASSAYS

A chromosome VII disome was used to measure chromosome loss. Yeast strain LS11 (MATα ade2 ade3 can1 CYH2$^R$ lys5 ura3-52 trp1Δ leu2-3,112 his3-200Δ) was transformed with HindIII cut pVS31, and a Ura$^+$ integrant was obtained that carried wild-type and pif1-m2 genes flanking the URA3 containing pRS306 plasmid. This strain was mated with the karogamy deficient strain LS15a (MATa kar1-1 ura3 aro2 leu2Δ), and LS11 cells that had received chromosome VII from LS15a were selected on YC plates containing canavanine and lacking lysine, tyrosine and arginine. One of these disomes was plated on FOA media to select for excision of a copy of pVS31, leaving either a wild-type or a mutant copy of PIF-1. This procedure yielded isogenic PIF-1 wild type and pif1-m2 chromosome VII disomes. These disomes were streaked on YEPD plates, grown and the colonies suspended in 1 ml of water. Aliquots were plated on YEPD plates containing cycloheximide and on YC plates lacking lysine and tyrosine and containing cycloheximide and 10 mg/l adenine. The chromosome loss, recombination and gene conversion rates were determined from 10 culture assays by the method of the median (Lea and Coulson, 1949, supra) essentially as described (Runge et al., 1991, supra). Standard deviations were determined according to Lea and Coulson, 1949, and were less than 29%.

EXAMPLE 1: ISOLATION OF MUTANTS

To identify genes that are important for telomere function, we screened for EMS-induced mutants that frequently lost expression of sub-telomeric genes. The sub-telomeric genes were carried on a 60.6 kbp yeast artificial chromosome called YAC-VS5 (FIG. 1). The URA3 gene was 2.6 kb from one telomere of YAC-VS5, and the ade3-2p gene was at the other telomere. Cells that express the URA3 gene product are able to grow on media lacking uracil, but are unable to grow on media containing 5-fluoro-orotic acid (FOA) (Boeke et al., 1984). The ade3-2p gene is a promoter-defective allele of the ADE3 gene (Koshland et al., 1985). Cells that are ade2 ade3 and that have zero, one or two copies of the ade3-2p gene are white, pink or red respectively. Although the constitutive level of expression of subtelomeric genes is often transcriptionally repressed (Gottschling et al., 1990), the URA3 and ade3-2p genes on YAC-VS5 are far enough away from a telomere that they are well expressed in wild-type cells (Table 1). YACVS5 also carried sequences required for stable chromosome maintenance (ARS1, CEN4, and two yeast telomeres), and a third selectable marker, LEU2, near the centromere. A tract of 108 base pairs of $C_4A_4/T_4G_4$ Oxytricha telomeric sequence was located directly proximal to the URA3 gene. The $C_4A_4/T_4G_4$ sequences support telomere formation in S. cerevisiae (Pluta et al., 1984). If the telomere near the URA3 gene were lost, the Oxytricha telomere sequence could potentially serve as a backup telomere and allow recovery of Leu$^+$, FOA resistant (FOA$^R$) colonies.

A three step procedure was used to identify mutants (FIG. 1). The first step enriched for mutants by selecting Leu$^+$ cells that were FOA$^R$, and therefore had reduced or no expression of the URA3 gene, but still contained the YAC. Next, these colonies were screened for loss of ade3-2p expression by searching for pink colonies with one or more white sectors. Finally, the FOA resistance phenotype of mutant candidates was retested with a new copy of YAC-VS5. The background of this system was low, since FOA$^R$, Leu$^+$ colonies were rarely seen in wild-type strains carrying YAC-VS5 (1.2×10$^{-6}$/cell/generation, see Table 1). Two of the mutations that were isolated, tst1-1 and tst1-2 (telomere stability) are the focus of this paper since they appeared to affect telomeres specifically.

EXAMPLE 2: PROPERTIES OF tst1 MUTANTS

The tst1-1 mutation caused a 146 fold increase in the rate of generation of Leu$^+$, FOA$^R$ colonies (see Table 1). The Leu$^+$, FOA$^R$ colonies could not grow on media lacking uracil, suggesting that the FOA resistance was not due to telomeric position effect repression of the URA3 gene. The tst1-1 mutation was a recessive nuclear mutation that segregated 2:2 after sporulation of a heterozygous diploid. Another independent mutation, tst1-2 caused the same phenotypes as tst1-1. Since tst1-1 did not complement tst1-2, these mutations were probably in the same gene.

Figure 2C:
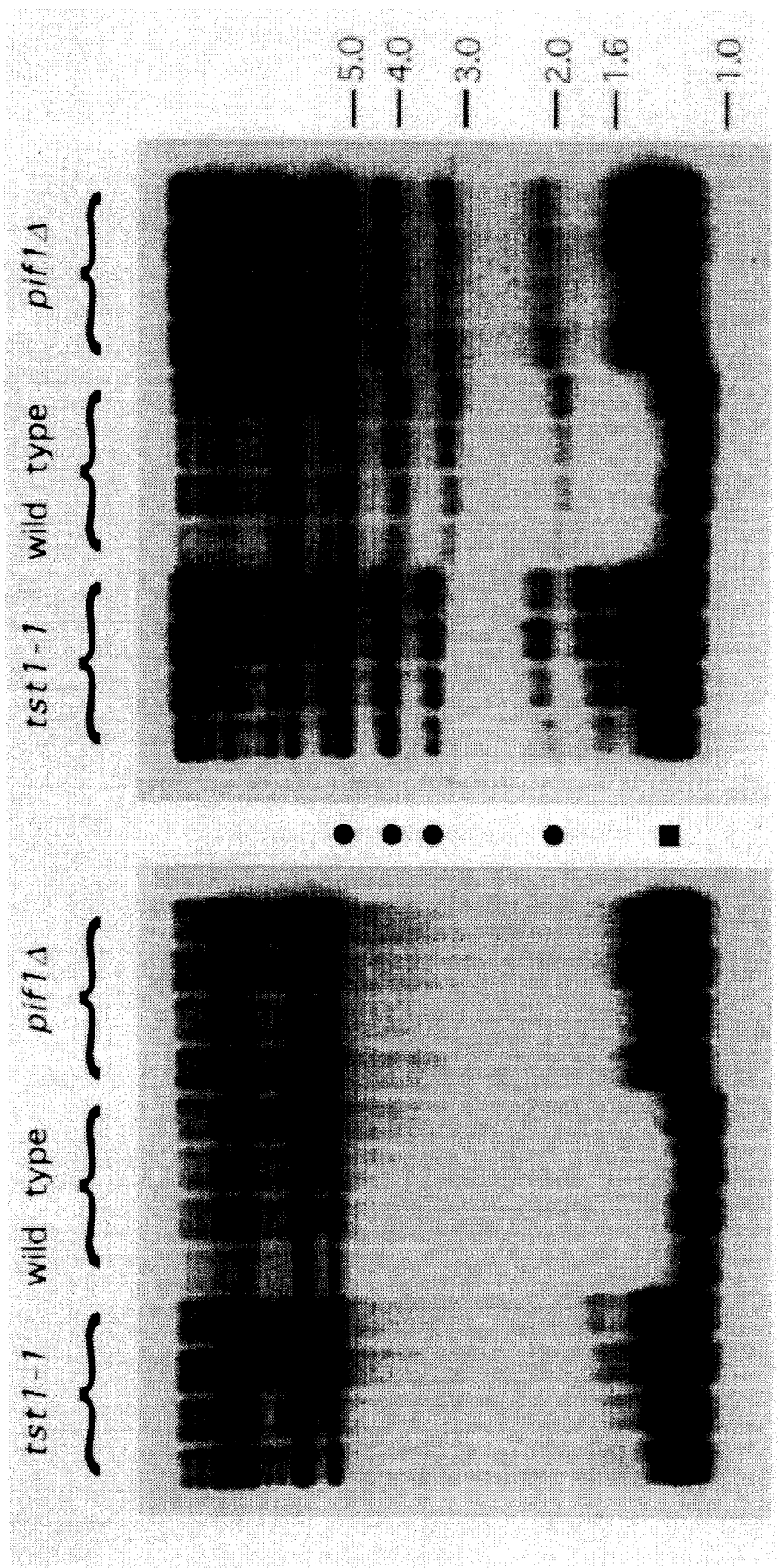
FIG. 2C shows the blot after it was stripped and hybridized with a $C_{1-3}A$ probe. Positions of size markers in kbp are shown at far right. Squares and circles at left indicate Y' and non-Y' telomeres respectively.

The effect of the tst1-1 mutation on telomere length was determined by Southern blot analysis of XhoI digested DNA (FIG. 2). Hybridization with a Y' subtelomeric probe showed that the tst1-1 mutation caused Y' telomeres to become about 75 bases longer. The distribution of telomere lengths was also wider in tst1-1 mutant cells. Hybridization of the same blot with a $C_{1-3}A$ telomeric probe showed that non-Y' telomeres also became longer and more heterogeneous (FIG. 2C). YAC-VS5 and chromosome I-R telomeres were similarly affected (data not shown).

The most easily scored phenotype of tst1-1 and tst1-2 cells was that colonies were smaller and heterogeneous in size. When small colonies were restreaked, only uniformly small colonies arose. Since the small colonies were unable to grow on media containing glycerol as a carbon source, they were deficient in respiration (i.e., petite). When larger (grande) colonies were restreaked, both grande and petite colonies were seen. These observations suggest that the tst1-1 mutation causes a defect in mitochondrial DNA maintenance. The mutation that affected mitochondria was identical or closely linked to the tst1-1 mutation, since the two phenotypes cosegregated in 48 random spores. tst1-1 cells had higher Leu$^+$, FOA resistance and longer telomeres than wild type cells even when glucose-grown petite, glucose-grown grande, and glycerol-grown grande cells were compared (data not shown). The telomere phenotype is therefore independent of mitochondrial function.

EXAMPLE 3: TST1 IS IDENTICAL TO PIF-1

The TST1 gene was cloned by searching for plasmids that reversed the slow growth phenotype of tst1-1 cells. We isolated two plasmids from a low copy number yeast library that caused tst1-1 cells to have stable mitochondria and short, homogeneous length telomeres. The two plasmids contained the same 10.8 kb insert. We subcloned restriction fragments from one of these plasmids and localized the TST1 gene by assaying complementation of the slow growth phenotype. A small region of DNA that was required for TST1 complementation was sequenced and compared to the Genbank DNA database using the PATMAT program (Henikoff et al., *Meth. Enz.* 183:111, 1990). The sequence was identical to a portion of a previously identified yeast gene, PIF-1. The restriction map of the cloned gene was also identical to that of PIF-1. These data lead us to conclude that the cloned gene that suppressed the tst1-1 phenotypes was PIF-1.

The PIF-1 gene was disrupted to determine if this change caused the same phenotype as the tst1-1 and tst1-2 mutations. Disruption of the PIF-1 gene also caused telomeres to be longer and more heterogeneous, and increased the production of Leu$^+$, FOA$^R$ colonies (FIG. 2 and Table 1). VPS105 cells with the PIF-1 deletion were unable to grow on glycerol media at 37° C. (data not shown), and frequently produced petite colonies at 30° C. (Table 1), like a previously described PIF-1 insertion strain (Van Dyck et al., *EMBO J.* 11:3421, 1992). The deletion mutation that we constructed was not able to complement the mitochondrial phenotype of a previously characterized PIF-1 insertion mutation (Van Dyck et al., 1992, supra), confirming that the gene that we cloned was PIF-1 (data not shown).

The PIF-1 deleted strain was mated to a tst1-1 strain to test if the tst1-1 mutation was in PIF-1. The pif1 Δ/tst1-1 heterozygote had the same phenotypes as the tst1-1 or pif1 strains. When this diploid was sporulated, 47 of 47 random spores tested had unstable mitochondria and increased production of Leu$^+$, FOA$^R$ colonies (data not shown). We conclude that the tst1-1 mutation is in the PIF-1 gene.

EXAMPLE 4: THE NUCLEAR AND MITOCHONDRIAL FUNCTIONS PIF-1 CAN BE SEPARATED BY MUTATION

Since PIF-1 mutations affected the maintenance of both nuclear and mitochondrial DNA, it seemed likely that Pif1p is in both compartments of the cell. Some proteins are targeted to two subcellular compartments by making two forms of the protein: a longer form goes to one compartment, and a shorter form goes to another (Rose et al., *Mol. Cell Biol.*, 12:5652, 1992 and references therein). We tested this possibility for PIF-1 by separately mutating the first (pif1 -m1) and second (pif1 -m2) methionines of the PIF-1 open reading frame to alanines. The first methionine is 39 amino acids from the second methionine. These mutations were introduced into the yeast genome by integrative transformation such that the only PIF-1 gene present was the mutant gene.

Mutation of the first methionine caused mitochondria to become unstable, but telomere length and production of Leu$^+$, FOA$^R$ colonies were wild type (FIG. 3). In contrast, mutation of the second methionine to produce only a longer, mutant form of Pif1p, caused telomeres to be longer and more heterogeneous, and an increased number of Leu$^+$ FOA$^R$ colonies Mitochondria were stable in the pif1 -m2 mutant. It was therefore possible to dissociate the mitochondrial and telomere phenotypes of PIF-1 by alterations of different AUG codons. Although the pif1 -m2 mutation did not affect telomeres as severely as a PIF-1 deletion, we used cells bearing the pif1 -m2 mutation for most of the following experiments because they grew as well as wild type cells.

EXAMPLE 5: FURTHER CHARACTERIZATION OF pif1 MUTANTS

Genes placed near yeast telomeres are subject to a reversible repression of transcription called telomere position effect repression (Gottschling et al., 1990). We tested if a pif1 mutation affected position effect repression by determining the frequency of FOA resistance when the URA3 gene was directly at the telomere of chromosome VII-L (not 2.6 kb away, as in the previous experiments). This experiment was carried out in two strains that have different levels of position effect repression. In wild type strains, the frequency of cells with URA3 repressed was 4.0% in strain VPS105 and 35% in strain YPH499. The frequency of position effect was 4.1% in strain VPS105 pif1 -m2 and 59% in strain YPH499 pif1 -m2. Therefore, the pif1 -m2 mutation does not significantly affect telomere position effect.

To determine how pif1 mutations caused loss of expression of the sub-telomeric genes on YAC-VS5, DNA was isolated from independent Leu$^+$, FOA$^R$ clones from both wild type and pif1 strains, digested with BstEII, and subjected to Southern blot analysis (FIG. 4). The blots were hybridized to pVZ1, λ and URA3 probes. Most (28/37) of the YACs from wild-type colonies had lost the URA3 gene, and a new yeast telomere had been added at the internal tract of $C_4A_4/T_4G_4$ DNA. All but one of the remaining Leu$^+$, FOA$^R$ YACs were indistinguishable from the original YAC-VS5 and were presumably due to point mutations in the URA3 gene (FIG. 4). In contrast, most (42/61) of the Leu$^+$, FOA$^R$ YACs from pif1 mutants had sustained large deletions extending into the bacteriophage λ sequences that comprise a large part of YAC-VS5 (FIG. 4). In many cases, a new heterogeneous length restriction fragment was seen that hybridized to both λ and $C_{1-3}$A probes. Therefore, the Leu$^+$, FOA$^R$ cells recovered in pif1 strains were due to physical loss of the end of the YAC, including loss of the URA3 gene and in most cases extending beyond the $C_4A_4/T_4G_4$ tract. These terminal deletions were associated with formation of a new telomere. In contrast to the situation in wild type cells, telomere formation did not usually occur at the internal $C_4A_4/T_4G_4$ tract. Nonetheless, although most of the Leu$^+$, FOA$^R$ YACs recovered in the pif1 strains had terminal deletions extending past the $C_4A_4/T_4G_4$ tract, the rate of telomere formation at the $C_4A_4/T_4G_4$ tract was still 250 times greater in the pif1 Δ strain than in wild type cells (FIG. 4B).

The effects of a PIF-1 mutation on copies of the URA3 gene placed at different locations on a natural chromosome were tested to determine if PIF-1 specifically affected telomeres (Table 2). When the URA3 gene was at its normal position near the centromere of chromosome V, the rate of FOA resistance was low in both a wild type and a pif1 -m2 strain. In wild-type cells, the rate of FOA resistance was also low when the URA3 gene was 2.6 kb from the telomere of chromosome VII-L. In contrast, the pif1 -m2 mutation increased the rate of FOA resistance of this telomere-linked URA3 gene 6.6 fold. In 8 of 8 cases, the FOA$^R$ phenotype was a consequence of physical loss of the URA3 gene (data not shown), with formation of a new telomere at the $C_4A_4/T_4G_4$ tract that is proximal to the URA3 gene. Thus, pif1 -m2 also increased the loss of a chromosomal URA3 gene but only when it was near a telomere. The sub-telomeric URA3 gene was lost at a higher rate from the YAC than from chromosome VII in wild type cells. Likewise, the pif1 -m2 mutation increased the loss of URA3 more from a YAC sub-telomeric region than from a chromosome VII subtelomeric region. The greater effects of pif1 -m2 on a YAC compared to a chromosomal copy of URA3 are probably explained by the fact that extensive terminal deletions from the left end of chromosome VII-L are expected to be lethal in haploid cells whereas over 44 kbp can be lost from the end of the YAC before LEU2 function would be affected.

EXAMPLE 6: THE INCREASED RECOVERY OF TERMINAL DELETIONS IN pif1 CELLS IS NOT A SECONDARY CONSEQUENCE OF EITHER AN INCREASE IN DOUBLE STRAND BREAKS OR OF LONG TELOMERES:

A possible mechanism for the increased recovery of terminal deletions in pif1 mutants is that the production of double-strand breaks throughout the genome is increased. According to this model, loss of an internal URA3 gene would not be elevated in pif1 cells because terminal deletions within or near an internal URA3 gene in a haploid cell would be lethal. Since double-strand breaks increase chromosome loss and recombination (Mortimer et al., *Proc. Natl. Acad. Sci.* 78:5778, 1981; Hartwell and Smith, *Genetics*, 110:381, 1985), we determined the effect of a pif1 mutation on chromosome loss, gene conversion and reciprocal recombination.

The pif1 -m2 mutation was introduced into an otherwise haploid strain that carried two copies of chromosome VII. In this strain, loss or recombination of one copy of chromosome VII can be monitored genetically (L. Sandell and V. Z., in prep, and FIG. 5). The pif1 -m2 mutation did not affect chromosome loss, gene conversion or reciprocal recombination (FIG. 5). Therefore, the effects of PIF-1 on telomere stability were not a consequence of a general increase in the generation of double strand breaks.

Figure 6A:
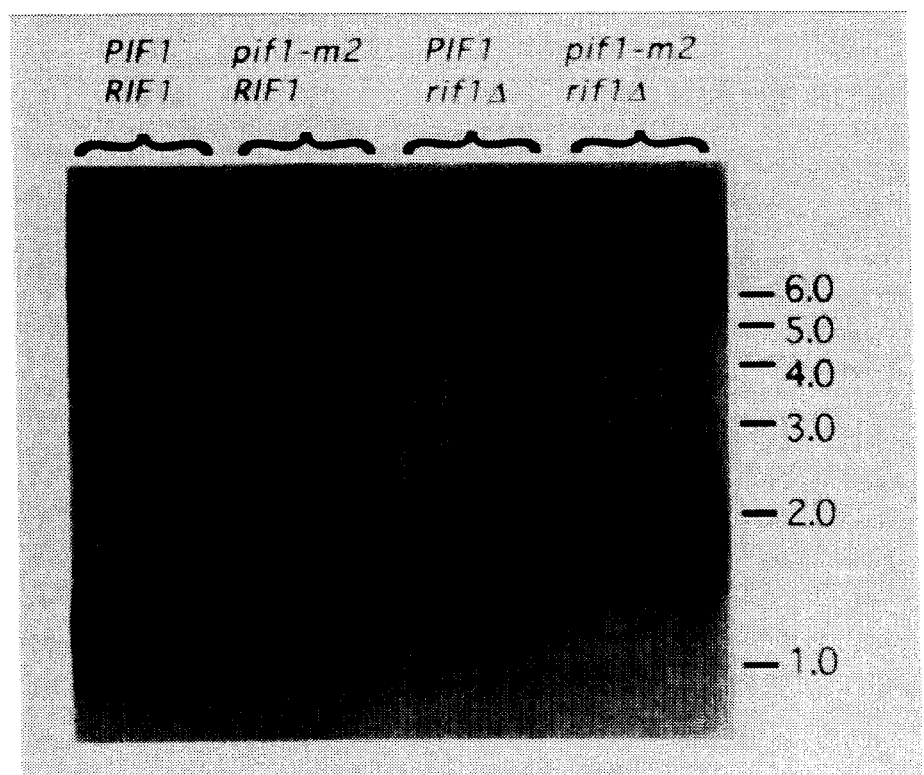
FIG. 6A shows mutations in PIF-1 and RIF1 have additive effects on telomere length. DNA was isolated from 3 separate cultures of each strain, cut with XhoI, run on a 1% agarose gel and analyzed by Southern blotting. The blot was hybridized with a Y' probe.

Another possibility is that the increased recovery of terminal deletions in pif1 cells is a secondary consequence of their long telomeres. To test this hypothesis, telomere length was increased in strain VPS105 by deleting the RIF1 gene. Deletion of RIF1 results in a 200–300 bp increase in telomere length (Hardy et al., 1992), which is greater than the ~75 bp increase associated with loss of PIF-1 function (FIG. 6A). Although deletion of RIF1 caused an increase in telomere length in VPS105 cells carrying YAC-VS5 (FIG. 6A), it did not cause an increase in the frequency of Leu$^+$, FOA$^R$ cells (FIG. 6B). Therefore, long telomeres were not sufficient to increase the rate of recovery of terminal deletions. RIF1 was also deleted in pif1 -m2 cells. Telomere length was longer in the double mutant than in either of the single mutants (FIG. 6A). Since the effects of the two mutations on telomere length were additive, the telomere lengthening caused by rif1 and pif1 -m2 probably occurs by two different pathways.

USE

Uses of modulators of PIF-1-type helicases are discussed above, but also include in vitro uses where modulators of helicases can be used in experimental procedures to study the effect of helicases on telomerases, as exemplified herein. In addition, such modulators can be used in laboratories to reduce the level of contamination by fungal cells, for example, in tissue culture media.

Preferably such modulators are targeted to the nucleus in which the PIF-1-type helicase is active, using standard procedures known to those in the art.

While analogous helicases can be readily identified as discussed above, such helicases can also be identified as described herein for Sacchromyces by generation of FOA resistant cells of other yeasts or of human cells. Such assays may be performed in vivo or in vitro.

Other embodiments are within the following claims.

---

We claim:

1. A method for identifying a modulator of telomere formation or elongation, comprising the steps of:

contacting a potential modulator of telomere formation or elongation with a PIF-1-type helicase in the presence of cells, and assaying the activity of said PIF-1-type helicase in vitro or in vivo, wherein said modulator specifically increases or decreases said activity and thereby modulates said telomere formation or elongation.

2. The method of claim 1, wherein the PIF-1-type helicase affects telomere function but not mitochondrial function.

3. The method of claim 1, wherein telomere length or heterogeneity are assayed to determine the activity of said PIF-1-type helicase.

4. The method of claim 3, wherein inhibition of activity of said PIF-1-type helicase is determined by an increase in telomere length.

5. The method of claim 1, wherein loss of subtelomeric genes is monitored to determine the activity of said PIF-1-type helicase.

6. The method of claim 1, wherein altered specificity of telomere formation is monitored to determine the activity of said PIF-1-type helicase.

7. The method of claim 1, wherein increased de novo telomere formation on a broken chromosome is monitored to determine the activity of said PIF-1-type helicase.

8. A modulator of telomere formation or elongation which specifically increases or decreases the activity Of PIF-1-type helicase, said modulator identified by the method of claim 1 that is specific for telomere function and not mitochondrial function.

* * * * *